(12) United States Patent
Park et al.

(10) Patent No.: US 10,751,002 B2
(45) Date of Patent: Aug. 25, 2020

(54) BIOSIGNAL PROCESSING APPARATUS AND METHOD

(71) Applicant: SAMSUNG ELECTRONICS CO., LTD., Suwon-si (KR)

(72) Inventors: Chang Soon Park, Chungju-si (KR); Ui Kun Kwon, Hwaseong-si (KR); Sang Joon Kim, Hwaseong-si (KR); Changmok Choi, Yongin-si (KR)

(73) Assignee: Samsung Electronics Co., Ltd., Suwon-si (KR)

( * ) Notice: Subject to any disclaimer, the term of this patent is extended or adjusted under 35 U.S.C. 154(b) by 124 days.

(21) Appl. No.: 15/212,556

(22) Filed: Jul. 18, 2016

(65) Prior Publication Data

US 2017/0027525 A1 Feb. 2, 2017

(30) Foreign Application Priority Data

Jul. 27, 2015 (KR) .................. 10-2015-0105568

(51) Int. Cl.
*A61B 5/00* (2006.01)
*G01R 29/26* (2006.01)
(Continued)

(52) U.S. Cl.
CPC .......... *A61B 5/7221* (2013.01); *A61B 5/7253* (2013.01); *G01R 29/26* (2013.01);
(Continued)

(58) Field of Classification Search
CPC . A61B 5/7221; A61B 5/7253; A61B 5/04004; A61B 5/0402; A61B 5/048; G01R 29/26
See application file for complete search history.

(56) References Cited

U.S. PATENT DOCUMENTS 4,680,708 A 7/1987 Ambos et al.
5,810,740 A * 9/1998 Paisner ................ A61B 5/6852
600/515
(Continued)

FOREIGN PATENT DOCUMENTS

CN 101933810 A 1/2011
CN 103781414 A 5/2014
(Continued)

OTHER PUBLICATIONS

Castells et al (Principal Component Analysis in ECG Signal Processing, Hindawi Publishing Corporation, EURASIP Journal on Advances in Signal Processing, vol. 2007, Article ID 74580, 21 (Year: 2007).*

(Continued)

*Primary Examiner* — Lisa E Peters
(74) *Attorney, Agent, or Firm* — NSIP Law

(57) ABSTRACT

A biosignal processing apparatus includes a communication interface configured to receive a biosignal, and a processor configured to set a target interval of the biosignal, calculate a quality metric corresponding to the target interval based on a target component that is a frequency component of the target interval corresponding to a set value and a non-target component that is a frequency component of the target interval not corresponding to the set value, and estimate a quality of the biosignal based on the quality metric.

16 Claims, 22 Drawing Sheets

(51) Int. Cl.
*A61B 5/048* (2006.01)
*A61B 5/0402* (2006.01)
*A61B 5/04* (2006.01)
*A61B 5/0488* (2006.01)

(52) U.S. Cl.
CPC ......... *A61B 5/0402* (2013.01); *A61B 5/04004* (2013.01); *A61B 5/048* (2013.01); *A61B 5/0488* (2013.01)

(56) References Cited

U.S. PATENT DOCUMENTS

| | | | |
|---|---|---|---|
| 7,828,740 | B2 | 11/2010 | Longhini et al. |
| 2004/0059237 | A1* | 3/2004 | Narayan ............ A61B 5/04525 600/509 |
| 2007/0239220 | A1 | 10/2007 | Greenhut et al. |
| 2008/0004811 | A1 | 1/2008 | Suzuki et al. |
| 2010/0079279 | A1 | 4/2010 | Watson et al. |
| 2011/0251505 | A1 | 10/2011 | Narayan et al. |
| 2012/0253140 | A1* | 10/2012 | Addison ............... A61B 5/4035 600/301 |
| 2012/0283581 | A1* | 11/2012 | Olde ........................ A61B 5/02 600/485 |
| 2012/0302900 | A1* | 11/2012 | Yin ....................... A61B 5/0205 600/484 |
| 2013/0085354 | A1* | 4/2013 | Hete ................... A61B 5/14551 600/323 |
| 2013/0245471 | A1* | 9/2013 | Baechler ............. A61B 5/0006 600/509 |
| 2013/0267796 | A1* | 10/2013 | Enric Monte Moreno .................. A61B 5/14532 600/301 |
| 2014/0073959 | A1* | 3/2014 | Rodriguez-Llorente .................... A61B 5/14551 600/479 |
| 2014/0107541 | A1* | 4/2014 | Sullivan ............... A61B 5/7217 601/41 |
| 2014/0275854 | A1* | 9/2014 | Venkatraman ......... A61B 5/721 600/301 |
| 2015/0173655 | A1* | 6/2015 | Demmer ............... A61B 5/1118 600/595 |
| 2015/0217119 | A1* | 8/2015 | Nikolski ............ A61N 1/36542 600/595 |
| 2016/0198969 | A1* | 7/2016 | Cheng .................. A61B 5/7203 600/511 |

FOREIGN PATENT DOCUMENTS

| | | |
|---|---|---|
| CN | 104720788 A | 6/2015 |
| EP | 1 196 862 | 4/2002 |
| KR | 10-2006-0078207 A | 7/2006 |
| KR | 10-1048763 B1 | 7/2011 |
| KR | 10-1307515 B1 | 9/2013 |
| KR | 10-1446183 B1 | 10/2014 |
| KR | 10-2014-0146782 A | 12/2014 |
| KR | 10-1503604 B1 | 3/2015 |
| WO | WO 2013/036718 A1 | 3/2013 |
| WO | WO 2015/055405 A1 | 4/2015 |

OTHER PUBLICATIONS

B Aldecoa Sanchez Del Rio et al: "Assessment of Different Methods to Estimate Electrocardiogram Signal Quality", 2011 Computing in Cardiology (CINC 2011) : Hangzhou, China, Sep. 18-21, 2011, IEEE, Piscataway, NJ, Sep. 18, 2011, pp. 609-612, XP032167341 (4 pages in English).

Luigi Yuri Di Marco et al: "Evaluation of an algorithm based on single-condition decision rules for binary classification of 12-lead ambulatory ECG recording quality", Physiological Measurement, Institute of Physics Publishing, Bristol, GB, vol. 33, No. 9, Aug. 17, 2012, pp. 1435-1448, XP020228803 (14 pages in English).

Extended European Search Report dated Jan. 2, 2017 in counterpart European Application No. 16161801.2. (10 pages in English).

Chinese Office Action dated Feb. 25, 2020 for the corresponding Chinese Patent Application No. 201610329407.8 (19 pages in English and 13 pages in Chinese).

\* cited by examiner

BIOSIGNAL PROCESSING APPARATUS AND METHOD

CROSS-REFERENCE TO RELATED APPLICATION(S)

This application claims the benefit under 35 USC 119(a) of Korean Patent Application No. 10-2015-0105568 filed on Jul. 27, 2015, in the Korean Intellectual Property Office, the entire disclosure of which is incorporated herein by reference for all purposes.

BACKGROUND

1. Field

The following description relates to a biosignal processing apparatus and a biosignal processing method.

2. Description of Related Art

Recently, due to an aging population structure, increasing medical costs, and a lack of personnel engaged in special medical services, research has been conducted on information technology (IT)-healthcare convergence technology in which IT is applied to medical technology. Thus, monitoring a health condition of an individual may be enabled anywhere, for example, at home and work, during daily life. For example, monitoring a health condition of a user may be enabled through mobile healthcare.

A biosignal may be used to monitor a health condition. The biosignal may be, for example, an electrocardiogram (ECG) signal, a photoplethysmogram (PPG) signal, or an electromyogram (EMG) signal. With ensured mobility and convenience of a biosignal measuring apparatus, monitoring a health condition may be performed more readily during daily life.

However, despite the ensured mobility of the biosignal measuring apparatus, correct measurement of a biosignal may not be possible due to a motion artifact that may be generated from, for example, an unstable external environment and a movement of a user.

SUMMARY

This Summary is provided to introduce a selection of concepts in a simplified form that are further described below in the Detailed Description. This Summary is not intended to identify key features or essential features of the claimed subject matter, nor is it intended to be used as an aid in determining the scope of the claimed subject matter.

In one general aspect, a biosignal processing apparatus includes a communication interface configured to receive a biosignal; and a processor configured to set a target interval of the biosignal, calculate a quality metric corresponding to the target interval based on a target component that is a frequency component of the target interval corresponding to a set value and a non-target component that is a frequency component of the target interval not corresponding to the set value, and estimate a quality of the biosignal based on the quality metric.

The processor may be further configured to convert the target interval to a frequency domain signal, and define, as the target component, a frequency component that is an integral multiple of the set value among frequency components of the frequency domain signal.

The processor may be further configured to extract from the target interval a first number of signals corresponding to the target component, and extract from the target interval a second number of signals corresponding to the non-target component; and the second number may be defined based on the first number and the set value.

The processor may be further configured to calculate the quality metric using an electric power of the extracted first number of signals and an electric power of the extracted second number of signals.

The processor may be further configured to change either one or both of the target interval and the set value after the calculating of the quality metric, calculate another quality metric different from the quality metric based on the changed either one or both of the target interval and the set value, and determine a first maximum quality metric among the quality metric and the other quality metric.

The processor may be further configured to determine a second maximum quality metric of another biosignal different from the biosignal, determine a maximum value among the first maximum quality metric and the second maximum quality metric, and determine a target interval corresponding to the maximum value to be a target biosignal to be monitored.

The processor may be further configured to determine whether the first maximum quality metric is greater than or equal to a threshold value, and determine a target interval corresponding to the first maximum quality metric to be a target biosignal to be monitored in response to a result of the determining being that the first maximum quality metric is greater than or equal to the threshold value.

The processor may be further configured to change the target interval by a first step size at least once to obtain at least one first changed target interval, calculate a quality metric corresponding to each of the at least one first changed target interval, select a target interval having a maximum quality metric among the target interval and the at least one first changed target interval, change the selected target interval by a second step size at least once to obtain at least one second changed target interval, calculate a quality metric corresponding to each of the at least one second changed target interval, and determine a first maximum quality metric based on the quality metric corresponding to the selected target interval and each of the at least one second changed target interval.

The processor may be further configured to determine the target interval to be a target biosignal to be monitored, and define a magnitude of a signal corresponding to the non-target component of the target interval to be a preset value.

The processor may be further configured to obtain period information of the target biosignal to be monitored.

In another general aspect, a biosignal processing apparatus includes a quality metric definer configured to define a quality metric based on a target component and a non-target component of a target interval of each biosignal of a plurality of biosignals; a quality estimator configured to estimate respective qualities of the biosignals based on the quality metric; and a determiner configured to determine a target biosignal to be monitored among the biosignals based on the qualities of the biosignals; and the target component may be a frequency component of the target interval corresponding to a set value, and the non-target component may be a frequency component of the target interval not corresponding to the set value.

The quality estimator may be further configured to obtain a representative quality metric of each biosignal; and the representative quality metric may be a maximum value of quality metrics of each biosignal that are obtained based on a change in either one or both of the target interval and the set value.

The determiner may be further configured to determine a target interval corresponding to a maximum value among the representative quality metrics to be the target biosignal to be monitored.

The quality estimator may be further configured to obtain quality metrics of each biosignal by changing at least either one or both of the target interval and the set value; and the determiner may be further configured to determine whether a representative quality metric of the quality metrics is greater than or equal to a threshold value, and determine a target interval corresponding to the representative quality metric to be the target biosignal to be monitored in response to a result of the determining being that the representative quality metric of the quality metrics is greater than or equal to the threshold value.

The quality estimator may be further configured to change the target interval by a first step size at least once to obtain at least one first changed target interval, calculate a quality metric corresponding to each of the at least one first changed target interval, select a target interval having a maximum quality metric among the target interval and the at least one first changed target interval, change the selected target interval by a second step size at least once to obtain at least one second changed target interval, calculate a quality metric corresponding to each of the at least one second changed target interval, and determine a maximum quality metric of each biosignal based on a quality metric corresponding to the selected target interval and each of the at least one second changed target interval.

The determiner may be further configured to define a magnitude of a signal corresponding to a non-target component of the determined target biosignal to be a preset value.

The determiner may be further configured to obtain period information of the determined target biosignal.

The quality metric definer may be further configured to convert the target interval to a frequency domain signal, and define a frequency component that is an integral multiple of the set value among frequency components of the frequency domain signal to be the target component.

The quality metric definer may be further configured to extract from the target interval a first number of signals corresponding to the target component, and extract from the target interval a second number of signals corresponding to the non-target component; and the second number may be defined based on the first number and the set value.

The quality metric definer may be further configured to define the quality metric using an electric power of the extracted first number of signals and an electric power of the extracted second number of signals.

In another general aspect, a biosignal processing method includes receiving a biosignal; setting a target interval of the biosignal; calculating a quality metric corresponding to the target interval based on a target component that is a frequency component of the target interval corresponding to a set value and a non-target component that is a frequency component of the target interval not corresponding to the set value; and estimating a quality of the biosignal based on the quality metric.

In another general aspect a biosignal processing method includes defining a quality metric corresponding to a target interval based on a target component and a non-target component of the target interval of each biosignal of a plurality of biosignals; estimating respective qualities of the biosignals based on the quality metric; and determining a target biosignal to be monitored among the biosignals based on the qualities of the biosignals; and the target component may be a frequency component of the target interval corresponding to a set value, and the non-target component may be a frequency component of the target interval not corresponding to the set value.

In another general aspect, a biosignal processing method includes receiving a biosignal; setting a plurality of target intervals of the biosignal; calculating quality metrics respectively corresponding to the target intervals; determine a maximum quality metric among the quality metrics; and determine the target interval corresponding to the maximum quality metric to be a biosignal to be monitored.

The setting of the plurality of target intervals of the biosignal may include setting a first target interval; changing the first target interval by a first step size at least once to obtain at least one first changed target interval; selecting one of the first target interval and the at least one first changed target interval having a maximum quality metric among quality metrics calculated for the first target interval and each of the at least one first changed target interval; changing the selected target interval at least once by a second step size smaller than the first step size to obtain at least one second changed target interval.

The determining of a maximum quality metric among the quality metrics may include determining a maximum quality metric among quality metrics calculated for the selected target interval and each of the at least one second changed target interval to be the maximum quality metric among the quality metrics.

The calculating of the quality metrics may include calculating each of the quality metrics based on at least one target component of a corresponding one of the target intervals and at least one non-target component of the corresponding one of the target intervals.

Each of the at least one target component may be a frequency component corresponding to an integral multiple of a set value; and each of the at least one non-target component may be a frequency component not corresponding to an integral multiple of the set value.

The set value may be an integer $R \geq 2$; a number of the at least one target component may be an integer $M \geq 1$; and a number of the at least one non-target component may be $M*(R-1)$.

The biosignal may be constituted by R repetitions of a basic waveform of the biosignal.

Other features and aspects will be apparent from the following detailed description, the drawings, and the claims.

BRIEF DESCRIPTION OF THE DRAWINGS

Throughout the drawings and the detailed description, the same drawing reference numerals refer to the same elements. The drawings may not be to scale, and the relative size, proportions, and depiction of elements in the drawings may be exaggerated for clarity, illustration, and convenience.

DETAILED DESCRIPTION

The following detailed description is provided to assist the reader in gaining a comprehensive understanding of the methods, apparatuses, and/or systems described herein. However, various changes, modifications, and equivalents of the methods, apparatuses, and/or systems described herein will be apparent to one of ordinary skill in the art. The sequences of operations described herein are merely examples, and are not limited to those set forth herein, but may be changed as will be apparent to one of ordinary skill in the art, with the exception of operations necessarily occurring in a certain order. Also, descriptions of functions and constructions that are well known to one of ordinary skill in the art may be omitted for increased clarity and conciseness.

The features described herein may be embodied in different forms, and are not to be construed as being limited to the examples described herein. Rather, the examples described herein have been provided so that this disclosure will be thorough and complete, and will convey the full scope of the disclosure to one of ordinary skill in the art.

The terminology used herein is for the purpose of describing particular examples only, and is not intended to limit the disclosure. As used herein, the singular forms "a," "an," and "the" are intended to include the plural forms as well, unless the context clearly indicates otherwise. As used herein, the terms "include," comprise," and "have" specify the presence of stated features, numbers, operations, elements, components, and/or combinations thereof, but do not preclude the presence or addition of one or more other features, numbers, operations, elements, components, and/or combinations thereof.

Unless otherwise defined, all terms, including technical and scientific terms, used herein have the same meaning as commonly understood by one of ordinary skill in the art to which this disclosure pertains. Terms, such as those defined in commonly used dictionaries, are to be interpreted as having a meaning that is consistent with their meaning in the context of the relevant art, and are not to be interpreted in an idealized or overly formal sense unless expressly so defined herein.

Figure 1:
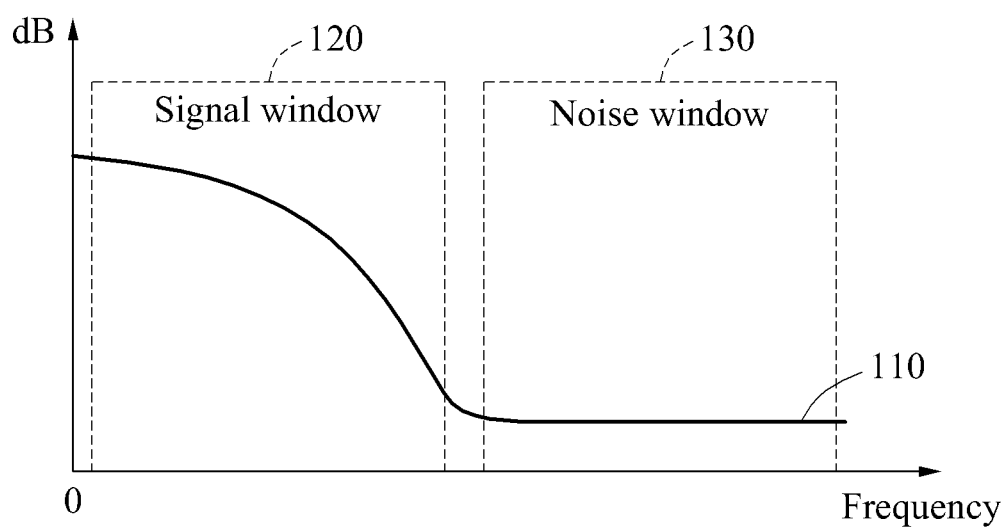
FIG. 1 is a diagram illustrating an example of biosignal processing.

FIG. 1 is a diagram illustrating an example of biosignal processing.

When a biosignal including a noise component is converted to a frequency domain signal 110 through a Fourier transform, a relatively high frequency component may be the noise component and a relatively low frequency component may be a desired signal.

In the example of FIG. 1, a signal window 120 corresponding to a frequency band of the desired signal and a noise window 130 corresponding to the noise component are illustrated. In this example, the signal window 120 does not include a direct current (DC) component.

To estimate a quality of the biosignal, a signal-to-noise ratio (SNR) of the frequency domain signal 110 may be used. The SNR may be defined based on a ratio of an electric power of a signal included in the signal window 120 to an electric power of a signal included in the noise window 130. In a method of estimating a quality of a biosignal based on an SNR, a distorted biosignal may be mistakenly determined to be a target biosignal to be monitored. Hereinafter, a detailed description will be provided with reference to FIGS. 2A and 2B.

Figure 2A:
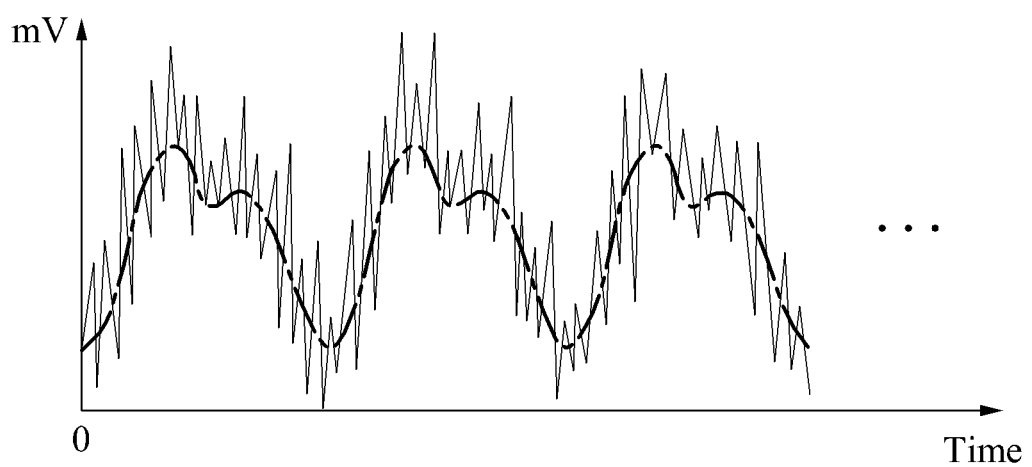
FIGS. 2A and 2B are diagrams illustrating examples of a biosignal.
Figure 2B:
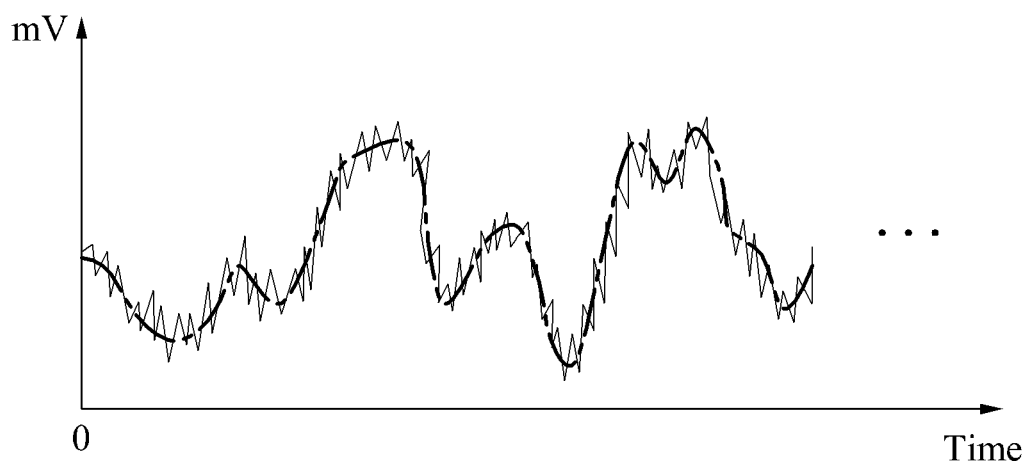

FIGS. 2A and 2B are diagrams illustrating examples of a biosignal.

In FIGS. 2A and 2B, different biosignals are illustrated, and a solid line indicates a biosignal including a noise component and a broken line indicates a biosignal from which the noise component has been eliminated.

Referring to FIGS. 2A and 2B, although average powers of the biosignals are at a similar level when the noise component is excluded, an average power of a noise component irregularly changing to a high frequency is higher in the example of FIG. 2A than in the example of FIG. 2B. When a quality of a biosignal is estimated using the method described with reference to FIG. 1, a quality of the biosignal illustrated in FIG. 2B in which the average power of the noise component is relatively small is estimated to be high. Thus, the biosignal illustrated in FIG. 2B is determined to be a target biosignal to be monitored.

A biosignal has periodicity. A biosignal sensed in a stable state, for example, when a user does not move, has periodicity even though the biosignal includes a noise component. However, in a situation in which, for example, a biosignal measuring apparatus is not a stable contact with a user, a sensed biosignal may not have periodicity. For example, although the quality of the biosignal illustrated in FIG. 2B is estimated to be higher than the quality of the biosignal illustrated in FIG. 2A according to the method described with reference to FIG. 1, the biosignal illustrated in FIG. 2B is not suitable for use as the target biosignal to be monitored because the biosignal illustrated in FIG. 2B does not have periodicity. Conversely, the biosignal illustrated in FIG. 2A is suitable for use as the target biosignal to be monitored despite its quality being estimated to be lower than the quality of the biosignal illustrated in FIG. 2B. Thus, the method described with reference to FIG. 1 is not suitable to estimate a quality of a biosignal.

Figure 3A:
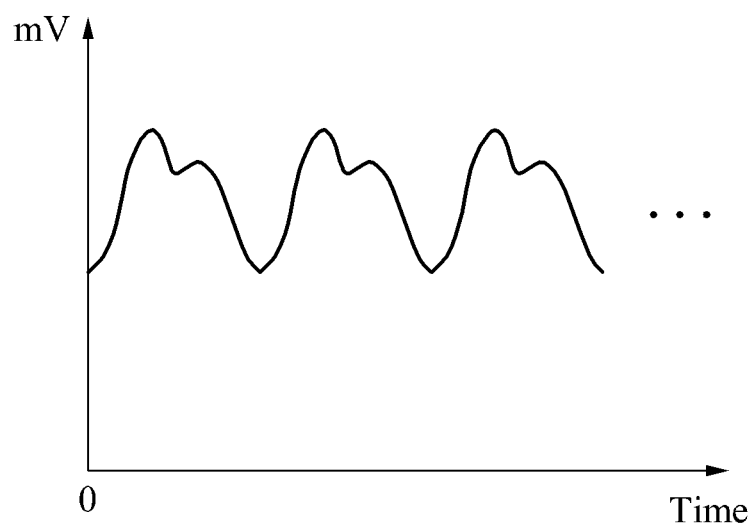
FIGS. 3A and 3B are diagrams illustrating another example of biosignal processing.
Figure 3B:
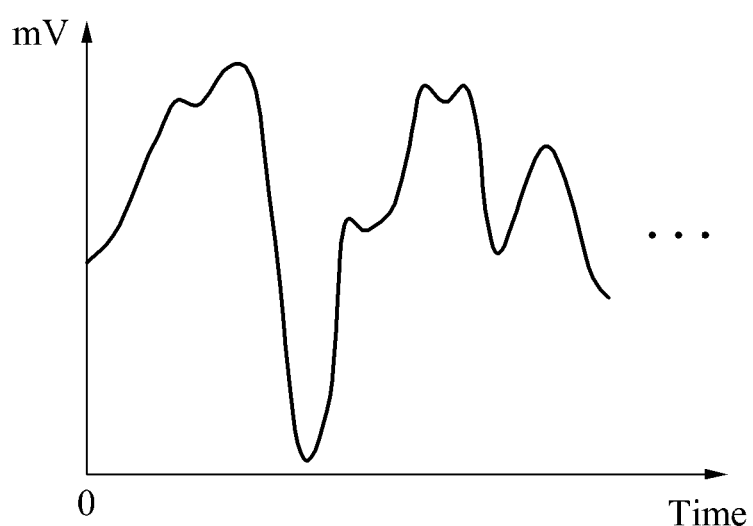

FIGS. 3A and 3B are diagrams illustrating another example of biosignal processing. In FIGS. 3A and 3B, a biosignal from which a noise component has been eliminated is illustrated. The noise component is a relatively high frequency component, and thus may be eliminated by a low-pass filter (LPF).

A variance, for example, a range of fluctuation, in the biosignal from which the noise component has been eliminated may be used to estimate a quality of the biosignal. An increase in a variance in strength, for example, an amplitude, of the biosignal indicates that the quality of the biosignal is higher. In such a case, a quality of the biosignal illustrated in FIG. 3B is estimated to be higher than a quality of the biosignal illustrated in FIG. 3A.

However, for the reasons described in the foregoing, the biosignal illustrated in FIG. 3B is not suitable for use as a target biosignal to be monitored because it does not have periodicity. Thus, a method using a variance in a biosignal is not suitable to estimate a quality of a biosignal.

FIGS. 4 through 10 are diagrams illustrating another example of biosignal processing.

Figure 4:
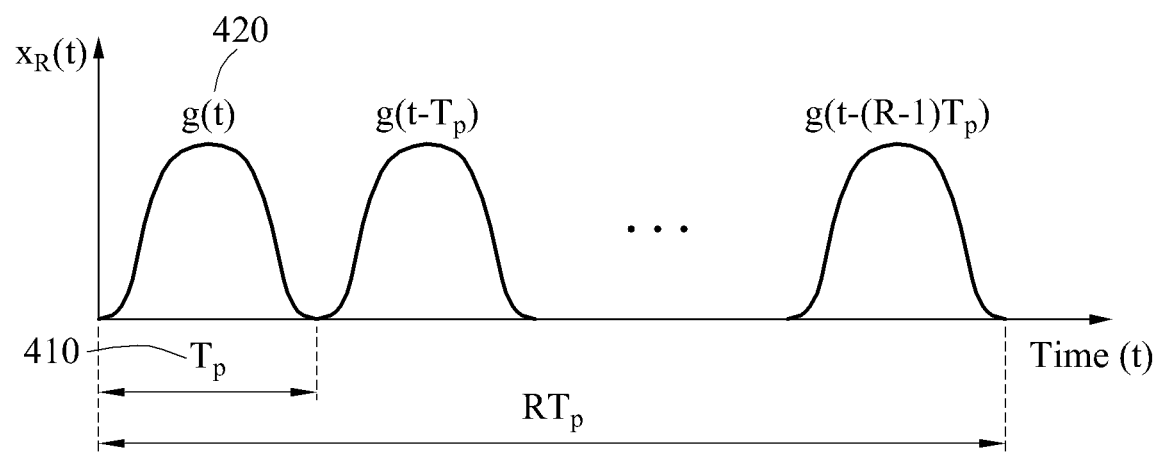
FIGS. 4 through 10 are diagrams illustrating another example of biosignal processing.

In FIG. 4, a desired biosignal $x_R(t)$ is illustrated. When a basic waveform g(t) 420 corresponding to a period $T_p$ 410 is repeated R times, a resulting time domain signal $x_R(t)$ may be expressed by Equation 1 below.

$$x_R(t) = \sum_{r=0}^{R-1} g(t - rT_p) = g(t) + g(t - T_p) + g(t - 2T_p) + \ldots + g(t - (R-1)T_p) \quad (1)$$

When $x_R(t)$ is converted to a frequency domain signal through a Fourier transform, a resulting frequency domain signal $X_R(f)$ may be expressed by Equation 2 below.

$$X_R(f) = \sum_{r=0}^{R-1} G(f)\exp(-j2\pi f(rT_p)) = G(f)\sum_{r=0}^{R-1} \exp(-j2\pi f(rT_p)) \quad (2)$$

In Equation 2, "G(f)" denotes $\int_{-\infty}^{\infty} g(t)\exp(-j2\pi ft)dt$. When an absolute value is applied to $$\sum_{r=0}^{R-1} \exp(-j2\pi f(rT_p)),$$

a number of zeros between neighboring peak values is R-1. Hereinafter, a detailed description will be provided with reference to FIG. 5.

Figure 5:
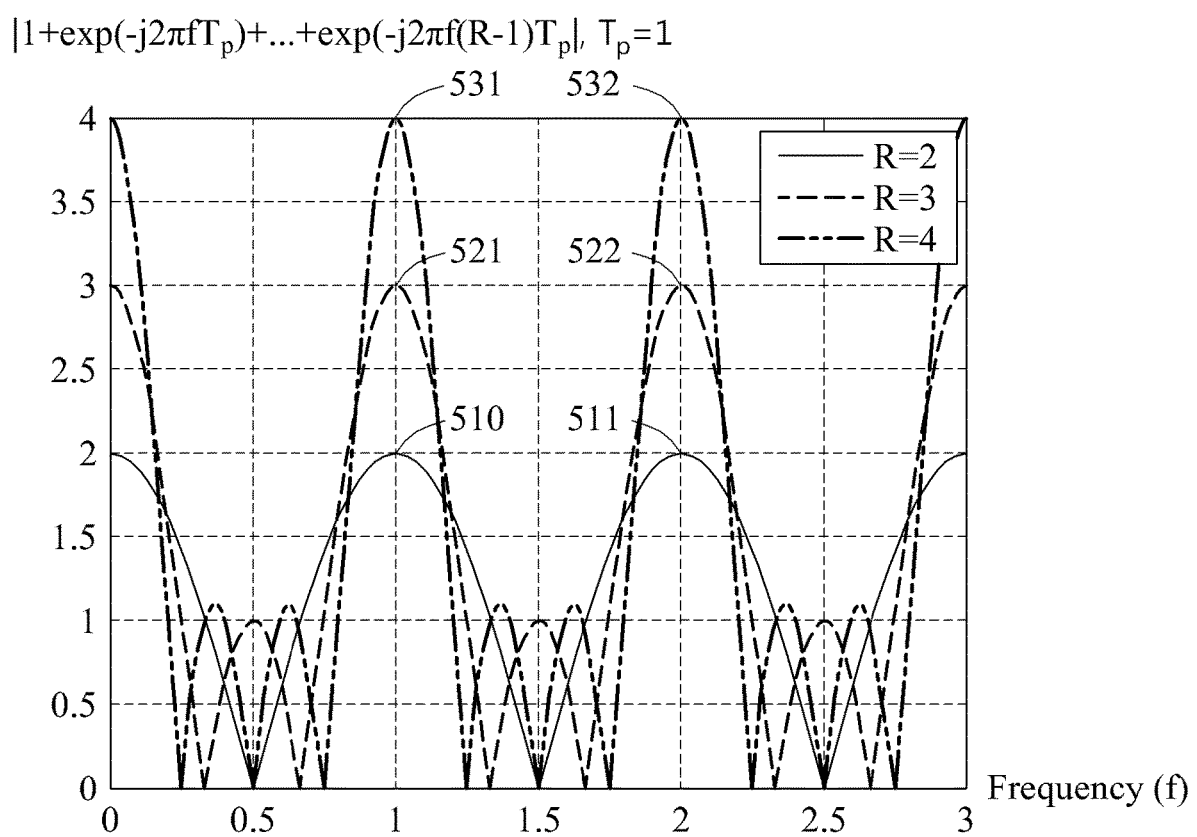

In FIG. 5, $$\left|\sum_{r=0}^{R-1} \exp(-j2\pi f(rT_p))\right|$$

based on a frequency is illustrated. Referring to FIG. 5, "$T_p$" is 1.

When "R," which is a constant, is 2, the number of frequency components having a magnitude of 0 between a peak value 510 and a peak value 511 is 1. When R is 3, the number of frequency components having a magnitude of 0 between a peak value 521 and a peak value 522 is 2. When R is 4, the number of frequency components having a magnitude of 0 between a peak value 531 and a peak value 532 is 3.

Based on the foregoing description provided with reference to FIG. 5, $X_R(f)$ may be expressed by Equation 3 below.

$$X_R(f) = \begin{cases} G(f) \cdot R, & \text{if } f = k/(RT_p) \text{ and } k = Rm \ (m: \text{integer}) \\ 0, & \text{if } f = k/(RT_p) \text{ and } k \neq Rm \ (m, k: \text{integer}) \\ G(f) \cdot (1 - \exp(-j2\pi fRT_p))/(1 - \exp(-j2\pi fT_p)), & \text{else} \end{cases} \quad (3)$$

In Equation 3, when "m" denotes an integer and a frequency f is $m/T_p$, $X_R(f) = G(f) \cdot R$. When f is $(Rm+1)/(RT_p)$, $(Rm+2)/(RT_p)$, ..., $(Rm+R-1)/(RT_p)$, present at equidistant intervals between $m/T_p$ and $(m+1)/T_p$, $X_R(f)=0$.

A biosignal sensed by a biosignal sensor may be a digital signal or a signal obtained by conversion to a digital signal, and thus a discrete Fourier transform (DFT) may be used for frequency analysis of the biosignal. Alternatively, a fast Fourier transform (FFT) with an increased operation speed compared to the DFT may be used for the frequency analysis of the biosignal. The DFT or FFT is applied to the biosignal to obtain a DFT result or an FFT result.

The DFT result or the FFT result may be obtained from $X_R(f)$. For example, the DFT result or the FFT result may be obtained from $X_R(f)$ using a value obtained by dividing a frequency domain sampling value in a continuous-time Fourier transform (CTFT) by a sampling interval. The sampling interval is an interval between time domain samples. The DFT result or the FFT result, $X_R[k]$, may be expressed by Equation 4 below.

$$X_R[k] = (1/T_s) \cdot X_R(f)|_{f=k/(NT_s)} = (1/T_s) \cdot X_R(f)|_{f=k/(RT_p)} \quad (4)$$

$$= \begin{cases} (1/T_s) \cdot R \cdot G(k/(RT_p)), & \text{for } k = Rm \ (m = 0, 1, 2, \ldots) \\ 0, & \text{else} \end{cases}$$

In Equation 4, "$T_s$" denotes a sampling interval, and "k" denotes an integer greater than or equal to 0 and less than or equal to N-1. The sampling interval is a time interval between the samples, or a distance between the samples. "N" denotes the number of all samples, and an FFT size or an FFT length.

In Equation 4, when k is not an integral multiple of R, $X_R[k]$ becomes 0. Conversely, when k is an integral multiple of R, $X_R[k]$ does not become 0. An example related to Equation 4 will be described in detail with reference to FIGS. 6A through 6D.

Figure 6A:
Figure 6B:
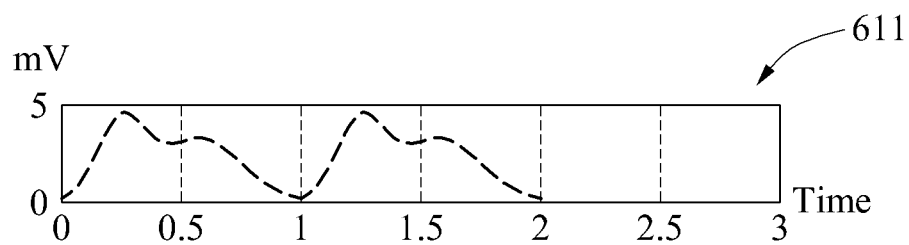
Figure 6C:
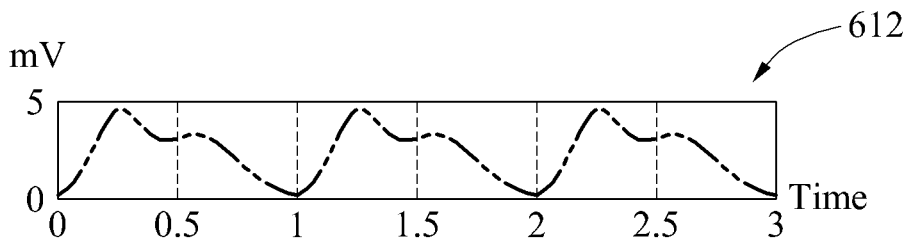
Figure 6D:
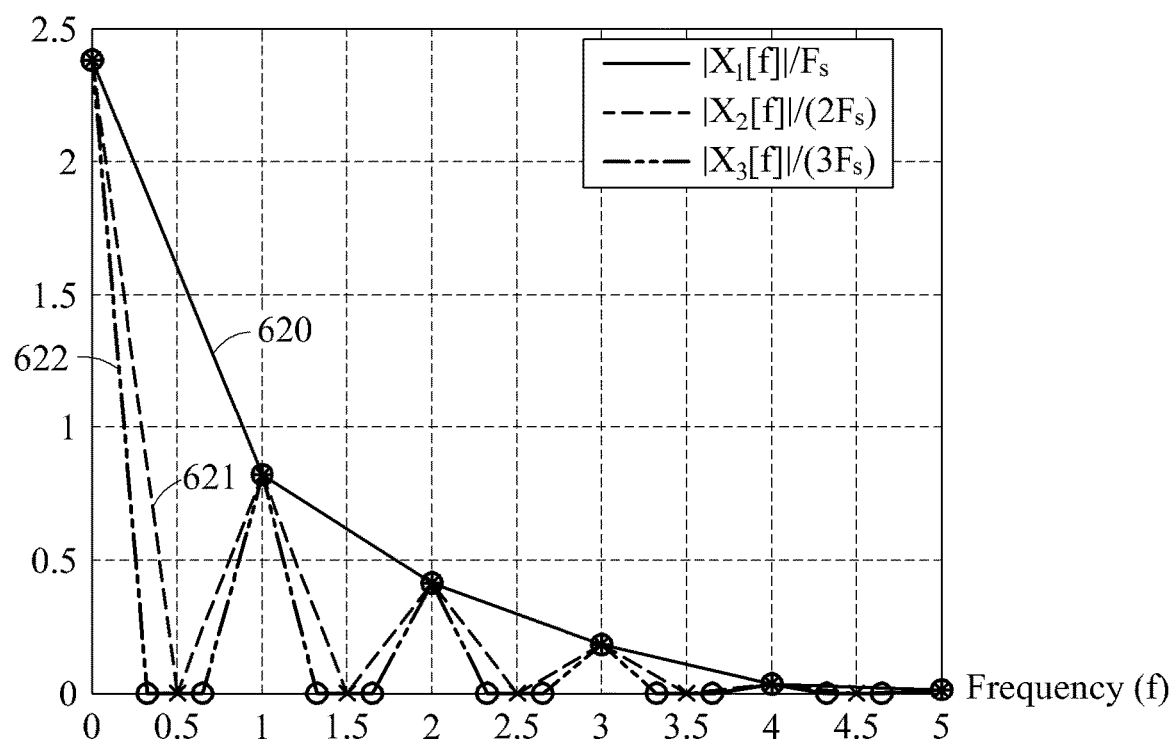

A time domain signal is illustrated in FIGS. 6A through 6C, and a frequency domain signal is illustrated in FIG. 6D. When a signal 610 of FIG. 6A is a basic waveform, a signal 611 of FIG. 6B is a signal in which the basic waveform is repeated two times and the number of waveform repetitions is 2, and a signal 612 of FIG. 6C is a signal in which the basic waveform is repeated three times and the number of waveform repetitions is 3.

Referring to FIG. 6D, the signal 610, the signal 611, and the signal 612 are converted to a signal 620, a signal 621, and a signal 622, respectively, through a DFT or an FFT. To normalize the signals 620 through 622, a DFT or FFT result is divided by $R*F_s$. "$F_e$" is an inverse value of $T_s$, and denotes a sampling rate. In the example of FIGS. 6A through 6D, $F_s$ is 250 hertz (Hz). In a graph of FIG. 6D, a horizontal axis indicates a frequency f. The vertical axis in the graph of FIG. 6D indicates a scaled value of k, for example, $k/(N*T_s)$.

In the signal 621, a magnitude of a signal corresponding to a first frequency component is 0, a magnitude of a signal corresponding to a second frequency component is not 0, a magnitude of a signal corresponding to a third frequency component is 0, and a magnitude of a signal corresponding to a fourth frequency component is not 0. Since the signal 611 is the signal in which the basic waveform is repeated twice, the signals corresponding to the second frequency component and the fourth frequency component of the signal 621 are a desired signal.

Similarly, in the signal 622, a magnitude of a signal corresponding to a first, a second, a fourth, and a fifth frequency component is 0, and a magnitude of a signal corresponding to a third and a sixth frequency component is not 0. Since the signal 612 is the signal in which the basic waveform is repeated three times, the signals corresponding to the third and the sixth frequency components are desired signals.

When a biosignal in which a basic waveform is repeated R times is converted to a frequency domain signal, a desired signal is distributed at a frequency component that is an integral multiple of R.

A desired biosignal and a frequency characteristic of the desired biosignal have been described in the foregoing. Hereinafter, a biosignal distorted by, for example, a noise component, a motion artifact, and white noise, and a frequency characteristic of the distorted biosignal will be described.

A biosignal including a noise component and other distortions may be expressed by Equation 5 below.

$$x_R(t) = \sum_{r=0}^{R-1} \{g(t-rT_p) + n_r(t-rT_p)\} \quad (5)$$
$$= g(t) + n_0(t) + g(t-T_p) + n_1(t-T_p) + g(t-2T_p) + n_2(t-2T_p) +$$
$$\ldots + g(t-(R-1)T_p) + n_{R-1}(t-(R-1)T_p)$$

In Equation 5, "$n_r(t-rT_p)$" denotes a non-repetitive component, which is a value based on a signal distortion. Although the waveform of $x_R(t)$ in Equation 1 differs from the waveform of $x_R(t)$ in Equation 5, the shapes of the waveforms are similar. Although $x_R(t)$ in Equation 5 is not a desired periodic signal due to the non-repetitive component, $x_R(t)$ in Equation 5 has an approximate periodicity. The number of approximately repeated waveforms in $x_R(t)$ in Equation 5 is R. The waveform of $x_R(t)$ in Equation 1 and the waveform of $x_R(t)$ in Equation 5 have a high correlation or similarity therebetween.

When the biosignal $x_R(t)$ of Equation 5 is sampled and a DFT or an FFT is applied to the sampled signal, a frequency domain signal $X_R[k]$ is obtained. $X_R[k]$ may be expressed by Equation 6 below.

$$X_R[k] = (1/T_s) \cdot X_R(f)|_{f=k/(NT_s)} = (1/T_s) \cdot X_R(f)|_{f=k/(RT_p)} \quad (6)$$
$$= \begin{cases} (1/T_s) \cdot \left[ R \cdot G(k/(RT_p)) + \sum_{r=0}^{R-1} N_r(k/(RT_p)) \right], \\ \quad \text{for } k = Rm \, (m = 0, 1, 2, \ldots) \\ (1/T_s) \cdot \sum_{r=0}^{R-1} N_r(k/(RT_p)) \exp(-j2\pi kr/R), \text{ else} \end{cases}$$

In Equation 6, "$N_r(f)$" is defined as $\int_{-\infty}^{\infty} n_r(t)\exp(-j2\pi ft)dt$. When a frequency component is not an integral multiple of R, $X_R[k]$ is not 0. $X_R[k]$ based on k is illustrated as a graph in FIG. 7. Hereinafter, a detailed description will be provided with reference to FIG. 7.

Figure 7:
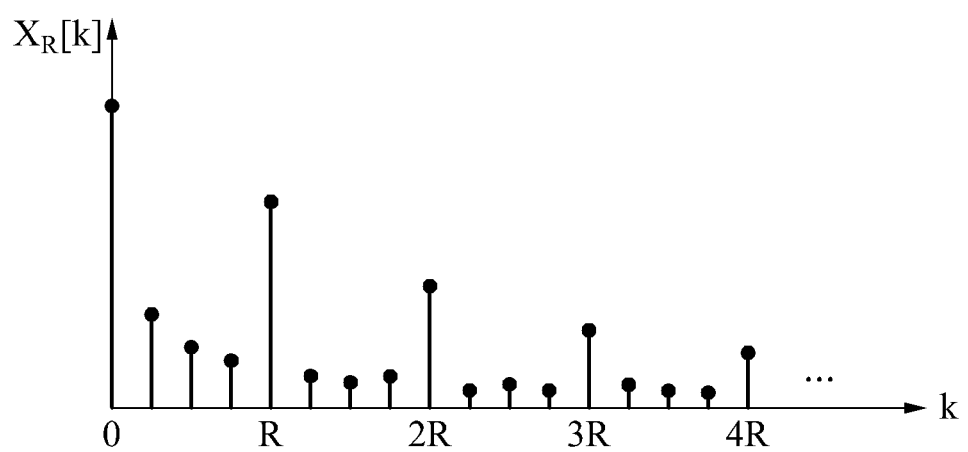

FIG. 7 illustrates a graph of $X_R[k]$ based on k.

When a waveform of a desired biosignal is repeated R times, a magnitude of a signal corresponding to a frequency component that is an integral multiple of R is large, and a frequency component that is not an integral multiple of R does not exist. Similarly, when a waveform of a biosignal including a non-repetitive component is repeated R times, a magnitude of a signal corresponding to a frequency component that is an integral multiple of R is large, and a magnitude of a signal corresponding to a frequency component that is not an integral multiple of R is small. As illustrated in FIG. 7, when a waveform of a biosignal including a non-repetitive component is repeated 4 times, a magnitude of a signal corresponding to a frequency component that is an integral multiple of 4 is larger than a magnitude of a signal corresponding to a frequency component that is not an integral multiple of 4.

In one example, a quality metric defined based on a frequency component corresponding to an integral multiple of R and a frequency component not corresponding to an integral multiple of R is used to estimate a quality of a biosignal. For example, the quality metric may be calculated based on an electric power, or a strength, of a signal corresponding to a frequency component that is an integral multiple of R, and an electric power, or a strength, of a signal corresponding to a frequency component that is not an integral multiple of R, and the quality of the biosignal may be estimated based on the quality metric. For example, when a waveform of a biosignal including a non-repetitive component is repeated R times, a quality metric of the biosignal will be large because a magnitude of a signal corresponding to a frequency component that is an integral multiple of R is greater than a magnitude of a signal corresponding to a frequency component that is not an integral multiple of R. A quality metric of a biosignal having a periodicity will be large, and a quality metric of a biosignal that does not have periodicity will be small.

The frequency components corresponding to integral multiples of R are referred to as target components, and the frequency components not corresponding to integral multiples of R are referred to as non-target components. In addition, a signal corresponding to the target component is referred to as a target component signal, and a signal corresponding to the non-target component is referred to as a non-target component signal. An example of a quality metric will be described with reference to FIG. 8.

Figure 8:
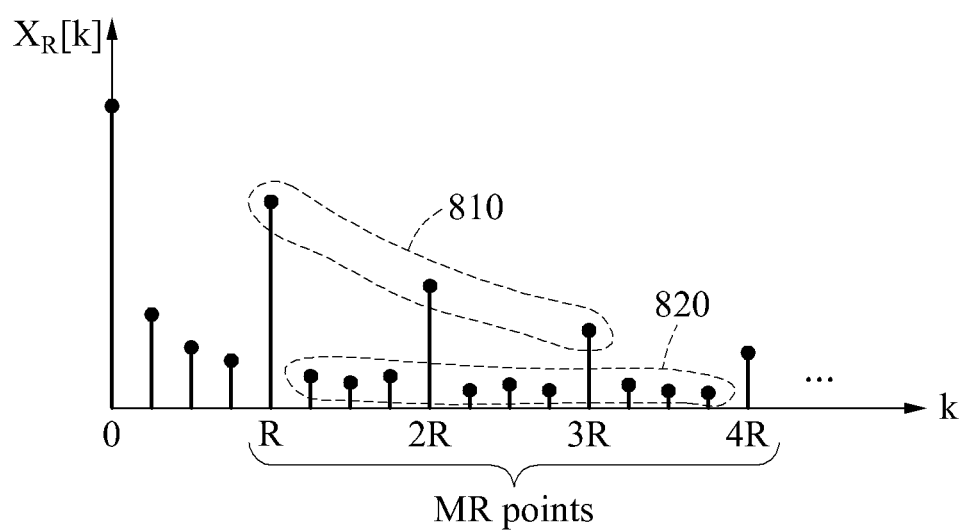

FIG. 8 illustrates an example of a quality metric.

Referring to FIG. 8, R−1 non-target components are distributed between a frequency component in which k is R and a frequency component in which k is 2R.

A quality metric $SNR_{RS}(M,R)$ may be defined as a ratio between a sum of electric powers of M target component signals 810 and a sum of electric powers of M*(R−1) non-target component signals 820. In such a case, the quality metric $SNR_{RS}(M,R)$ may be expressed by Equation 7 below.

$$SNR_{RS}(M, R) = \frac{\sum_{m=1}^{M} |X_R[Rm]|^2}{\sum_{m=1}^{M} \sum_{l=1}^{R-1} |X_R[Rm+l]|^2} \quad (7)$$

Figure 9A:
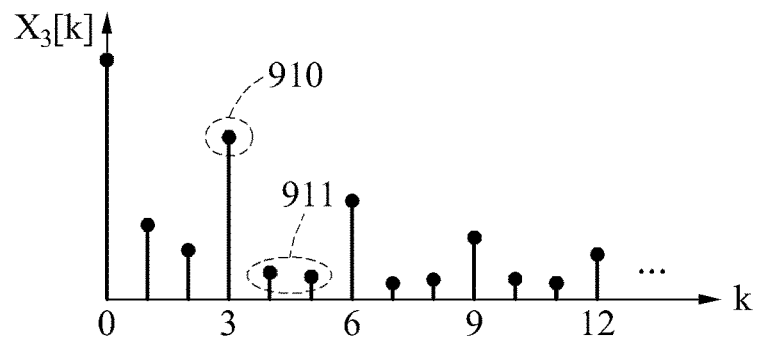

Examples of calculating the quality metric based on Equation 7 are illustrated in FIGS. 9A through 9O.

Figure 9B:
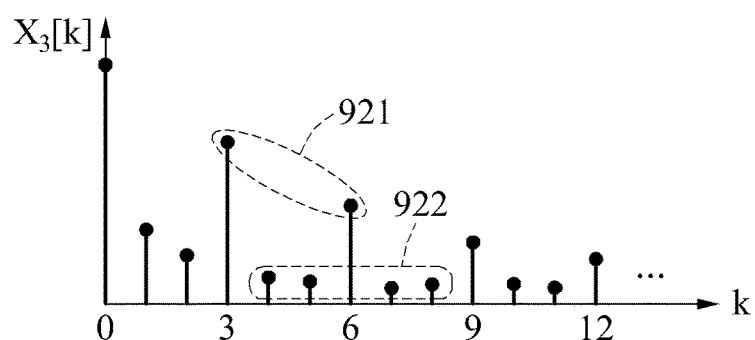
Figure 9C:
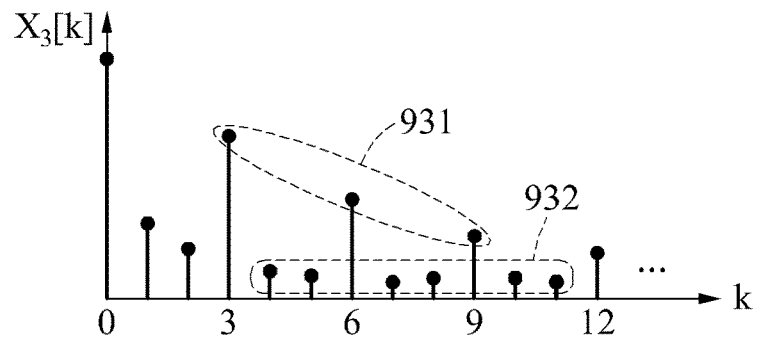

In the examples of FIGS. 9A through 9C, R is 3. FIG. 9A illustrates an example of a quality metric $SNR_{RS}(1,3)$ in which M is 1, FIG. 9B illustrates an example of a quality metric $SNR_{RS}(2,3)$ in which M is 2, and FIG. 9C illustrates an example of a quality metric $SNR_{RS}(3,3)$ in which M is 3. M denotes the number of target components.

In the example of FIG. 9A, an electric power of a target component signal 910 and an electric power of a non-target component signal 911 are used to calculate a quality metric. A non-target component to be used to calculate the quality metric is a frequency component distributed on a right side of a target component.

In the example of FIG. 9B, an electric power of a target component signal 921 and an electric power of a non-target component signal 922 are used to calculate a quality metric. The number of target components is 2, and a non-target component is a frequency component distributed on a right side of each of the two target components. When a target component in which k is 3 is a reference component, a frequency component in which k is 4 and 5 is a non-target component corresponding to the reference component. When a target component in which k is 6 is a reference component, a frequency component in which k is 7 and 8 is a non-target component corresponding to the reference component.

In the example of FIG. 9C, an electric power of a target component signal 931 and an electric power of a non-target component signal 932 are used to calculate a quality metric. The number of target components is 3, and a non-target component is a frequency component distributed on a right side of each of the three target components.

As described in the foregoing, a quality metric may be calculated using an electric power of a target component signal and an electric power of a non-target component signal distributed on a right side of the target component signal.

The examples described with reference to FIGS. 9A through 9C are provided as illustrative examples only, and thus a quality metric is not limited to the examples described with reference to FIGS. 9A through 9C. Hereinafter, another example of a quality metric will be described with reference to FIG. 10.

Figure 10:
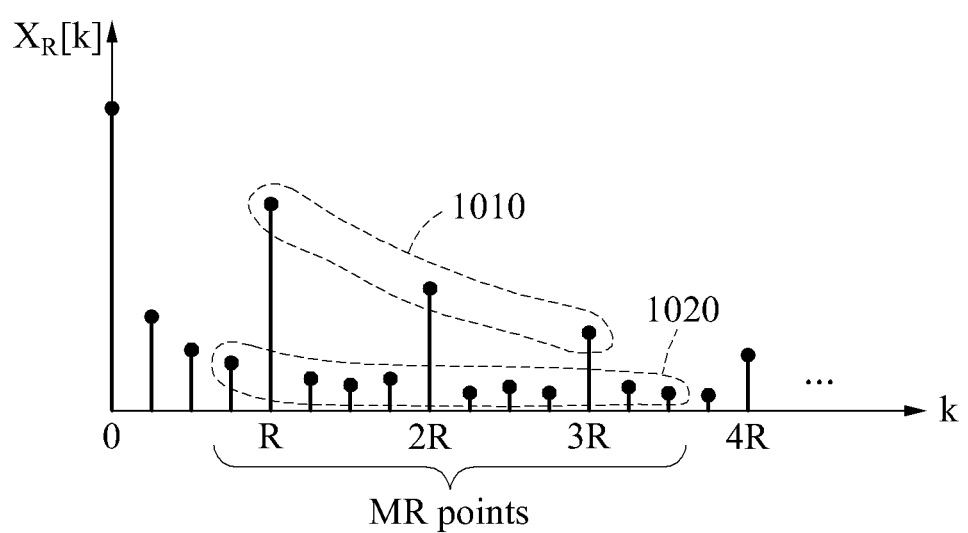

FIG. 10 is a diagram illustrating another example of a quality metric.

Dissimilar to the examples illustrated in FIGS. 9A through 9C, a non-target component to be used to calculate a quality metric is a frequency component distributed on a left side of a target component and a frequency component distributed on a right side of the target component. In the example of FIG. 10, when a target component in which k is R is a reference component, one frequency component distributed on a left side of the reference component and two frequency components distributed on a right side of the reference component are a non-target component corresponding to the reference component. Similarly, when a target component in which k is 2R is a reference component, a 2R−1 frequency component, a 2R+1 frequency component, and a 2R+2 frequency component are a non-target component corresponding to the reference component. Another example of the quality metric illustrated in FIG. 10 may be expressed by Equation 8 below.

$$SNR_{RS}(M, R) = \frac{\sum_{m=1}^{M} |X_R[Rm]|^2}{\sum_{m=1}^{M} \left( \sum_{l=1}^{L_{left}} |X_R[Rm-l]|^2 + \sum_{l=1}^{L_{right}} |X_R[Rm+l]|^2 \right)} \quad (8)$$

In Equation 8, "$L_{left}$" and "$L_{right}$" denote an integer, and $L_{left}+L_{right}=R-1$.

As illustrated in FIG. 10, the quality metric may be calculated based on an electric power of a target component signal 1010 and an electric power of a non-target component signal 1020.

Although not illustrated in FIG. 10, in one example, a quality metric is calculated using a maximum electric power of an electric power of a non-target component. In another example, a quality metric is calculated based on a sum of an electric power of M target component signals and the maximum electric power of the electric power of the non-target component signal. Still another example of a quality metric may be expressed by Equation 9 below.

$$SNR_{RS}(M, R) = \frac{\sum_{m=1}^{M} |X_R[Rm]|^2}{M(R-1) \cdot \max_{\substack{1 \le m \le M, \\ 1 \le l \le R-1}} |X_R[Rm+l]|^2} \quad (9)$$

A non-target component having the maximum electric power is identified, and the sum of the electric power of the M target component signals in comparison to a value of M*(R−1)*maximum electric power is calculated as the quality metric. In addition, dissimilar to Equation 9, a quality metric may be calculated using a maximum electric power or a minimum electric power of the electric power of the target component signals. For example, a value of M*maximum electric power in comparison to a sum of the electric power of the non-target component signal may be calculated as the quality metric. In addition, the sum of the electric power of the M target component signals in comparison to M*(R−1)*minimum electric power may be calculated as the quality metric. The minimum electric power is a minimum electric power of the electric power of the non-target component signal.

The examples described with reference to FIG. 10 are provided as illustrative examples only, and thus a quality metric is not limited to the examples described with reference to FIG. 10.

Figure 11:
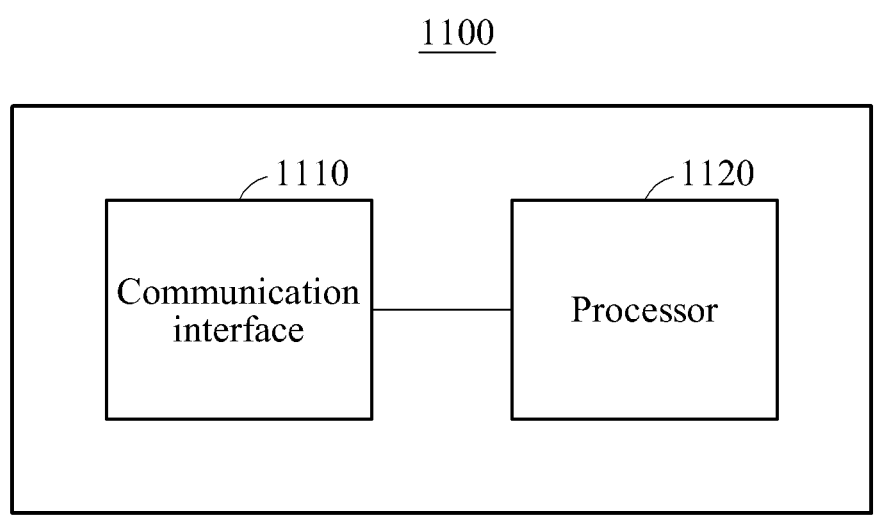
FIG. 11 is a diagram illustrating an example of a biosignal processing apparatus.

FIG. 11 is a diagram illustrating an example of a biosignal processing apparatus 1100.

Referring to FIG. 11, the biosignal processing apparatus 1100 includes a communication interface 1110 and a processor 1120.

The communication interface 1110 receives a biosignal. For example, the communication interface 1110 includes an input port and an output port of the processor 1120. The communication interface 1110 receives the biosignal sensed by a sensor through a bus (not shown), and the processor 1120 receives the biosignal from the communication interface 1110.

The processor 1120 sets a target interval of the biosignal. The target interval is an interval that is set to calculate a quality metric to be used to estimate a quality of the biosignal. As described hereinafter, the target interval is a target biosignal to be monitored. The processor 1120 sets, as the target interval, a biosignal included between a first point and a second point. In addition, the target interval may be set based on a characteristic of the biosignal. For example, a normal heart rate range is 60 to 100 beats per minute, and the processor 1120 may set the target interval based on the normal heart rate range. In addition, the processor 1120 may also set the target interval based on an abnormal range deviating from the normal heart rate range in addition to the normal heart rate range. The abnormal range may be a preset range.

The processor 1120 calculates a quality metric corresponding to the target interval based on a target component and a non-target component. The target component is a frequency component corresponding to a set value among frequency components of the target interval, and the non-target component is a frequency component not corresponding to the set value among the frequency components of the target interval.

When the target interval is set, the processor 1120 converts the target interval to a frequency domain signal. For example, the biosignal input from the communication interface 1110 is a sampled biosignal, and thus the processor 1120 applies a DFT or an FFT to the biosignal input from the communication interface 1110.

The processor 1120 defines, as the target component, a frequency component that is an integral multiple of the set value among frequency components of the frequency domain signal. Also, the processor 1120 defines, as the non-target component, a frequency component that is not an integral multiple of the set value.

The processor 1120 extracts a first number of target component signals, and extracts a second number of non-target component signals. The second number is defined based on the first number and the set value. When the first number is M and the set value is R, a value of the second number is M*(R−1). The processor 1120 calculates a quality metric using an electric power of the extracted first number of signals and an electric power of the extracted second number of signals, and the quality metric may be expressed by Equation 10 or 11 below.

$$SNR_{RS}(M, R) = \frac{\sum_{m=1}^{M} |X_R[Rm]|^2}{\sum_{m=1}^{M} \sum_{l=1}^{R-1} |X_R[Rm+l]|^2} \quad (10)$$

$$SNR_{RS}(M, R) = \frac{\sum_{m=1}^{M} |X_R[Rm]|^2}{\sum_{m=1}^{M} \left( \sum_{l=1}^{L_{left}} |X_R[Rm-l]|^2 + \sum_{l=1}^{L_{right}} |X_R[Rm+l]|^2 \right)} \quad (11)$$

In Equation 11, the portion of the denominator $$\sum_{l=1}^{L_{left}} |X_R[Rm-l]|^2$$

denotes an electric power of a non-target component signal distributed on a left side of a target component signal, and the portion of the denominator $$\sum_{l=1}^{L_{right}} |X_R[Rm+l]|^2$$

denotes an electric power of a non-target component signal distributed on a right side of the target component signal.

In addition, the processor 1120 may calculate the quality metric using a maximum electric power of the electric power of the non-target component signal and the electric power of the target component signal, and the quality metric may be expressed by Equation 12 below.

$$SNR_{RS}(M, R) = \frac{\sum_{m=1}^{M} |X_R[Rm]|^2}{M(R-1) \cdot \max_{\substack{1 \le m \le M, \\ 1 \le l \le R-1}} |X_R[Rm+l]|^2} \quad (12)$$

The processor 1120 changes either one or both of the target interval and the set value after the quality metric is calculated. To change the target interval, the processor 1120 expands the target interval. Expanding the target interval means setting a new target interval. The processor 1120 sets a new target interval that is temporally different from the target interval. In addition, to change the set value, the processor 1120 increases or decreases the set value. The processor 1120 changes the set value R without changing the target interval.

The processor 1120 calculates another quality metric different from the quality metric based on the change in the either one or both of the target interval and the set value. The processor 1120 calculates a quality metric corresponding to the changed target interval. In addition, the processor 1120 calculates the other quality metric using the changed set value. For example, the processor 1120 calculates $SNR_{RS}$(M,R) when R is 2, and $SNR_{RS}$(M,R) when R is 3. In another example, the processor 1120 calculates a different quality metric by changing values of M and R. In another example, the processor 1120 calculates the other quality metric different from the quality metric by changing the set value and the target interval.

The examples of calculating the other quality metric described in the foregoing are provided as illustrative examples only, and thus calculating another quality metric is not limited to the foregoing description.

The processor 1120 estimates a quality of the biosignal based on the quality metric. The processor 1120 determines a first maximum quality metric based on the quality metric and the other quality metric. The first maximum quality metric is a maximum value among the quality metric and the other quality metric. The processor 1120 stores, in a memory, the first maximum quality metric. In addition, the processor 1120 stores, in the memory, identification information of a target interval corresponding to the first maximum quality metric, for example, an index of a starting sample and an index of a ending sample of the target interval.

In one example, the processor 1120 receives another biosignal, hereinafter referred to as a second biosignal, that is different from the biosignal, hereinafter referred to as a first biosignal. A sensing channel of the second biosignal is different from a sensing channel of the first biosignal. Alternatively, the second biosignal is sensed at a time different from a time at which the first biosignal is sensed. The sensing channel of the second biosignal and/or a time interval at which the second biosignal is sensed differ from the sensing channel of the first biosignal and/or a time interval at which the first biosignal is sensed. The processor 1120 estimates a quality of the second biosignal using a method identical to a method of estimating a quality of the first biosignal. The processor 1120 determines a target biosignal to be monitored based on the quality of the first biosignal and the quality of the second biosignal.

In one example, the processor 1120 calculates a plurality of quality metrics of the second biosignal, and determines a second maximum quality metric among the quality metrics. The second maximum quality metric is a maximum value among the quality metrics. When the second maximum quality metric is determined, the processor 1120 determines a maximum value among the second maximum quality metric and the first maximum quality metric. The processor 1120 determines, to be the target biosignal to be monitored, a target interval corresponding to the maximum value.

In another example, the processor 1120 determines whether the first maximum quality metric is greater than or equal to a threshold value. When the first maximum quality metric is greater than or equal to the threshold value, the processor 1120 determines, to be the target biosignal to be monitored, a target interval corresponding to the first maximum quality metric. When the target biosignal to be monitored is determined, the processor 1120 suspends obtaining the second maximum quality metric. In such a case, the processor 1120 generates a control signal to provide an instruction of the suspension of the obtaining of the second maximum quality metric. When the first maximum quality metric is less than the threshold value, the processor 1120 determines whether the second maximum quality metric is greater than or equal to the threshold value. When the second maximum quality metric is less than the threshold value, the processor 1120 compares a maximum quality metric of yet another biosignal to the threshold value to determine the target biosignal to be monitored. When a maximum quality metric of each of sensed biosignals is less than the threshold value, the processor 1120 generates a control signal to provide an instruction of sensing a biosignal. The biosignals are sensed based on the control signal.

In one example, the processor 1120 defines, as a preset value, a magnitude of a non-target component signal of the determined biosignal. For example, the processor 1120 defines, as 0, the magnitude of the non-target component signal so that the determined biosignal does not have a non-target component. Since the determined biosignal is a frequency domain signal, the processor 1120 converts the determined biosignal to a time domain signal. For example, the processor 1120 converts the determined biosignal to the time domain signal by applying an inverse fast Fourier transform (IFFT) to the determined biosignal. When the magnitude of the non-target component signal is defined as 0, the time domain signal obtained by the converting is a signal from which a noise component is eliminated.

The target biosignal determined to be monitored is transmitted to an external device through a communicator. The communicator may be included in the biosignal processing apparatus 1100. Alternatively, the communicator may be a device physically separate from the biosignal processing apparatus 1100 and located outside the biosignal processing apparatus 1100. The biosignal processing apparatus 1100 controls the communicator to transmit the target biosignal determined to be monitored to the external device. A communication method supported by the communicator may include, for example, a wireless local area network (WLAN) method, a Wi-Fi method, a digital living network alliance (DLNA) method, a wireless broadband (WiBro) method, a worldwide interoperability for microwave access (WiMAX) method, a high-speed downlink packet access (HSDPA) method, a Bluetooth method, a radio-frequency identification (RFID) method, an infrared data association (IrDA) method, an ultra-wideband (UWB) method, a ZigBee method, and a near field communication (NFC) method. The biosignal transmitted to the external device may be monitored, and thus health information of a user may be obtained through the monitoring.

The descriptions provided with reference to FIGS. 1 through 10 are also applicable to FIG. 11, and thus a more detailed description of FIG. 11 has been omitted.

Figure 12:
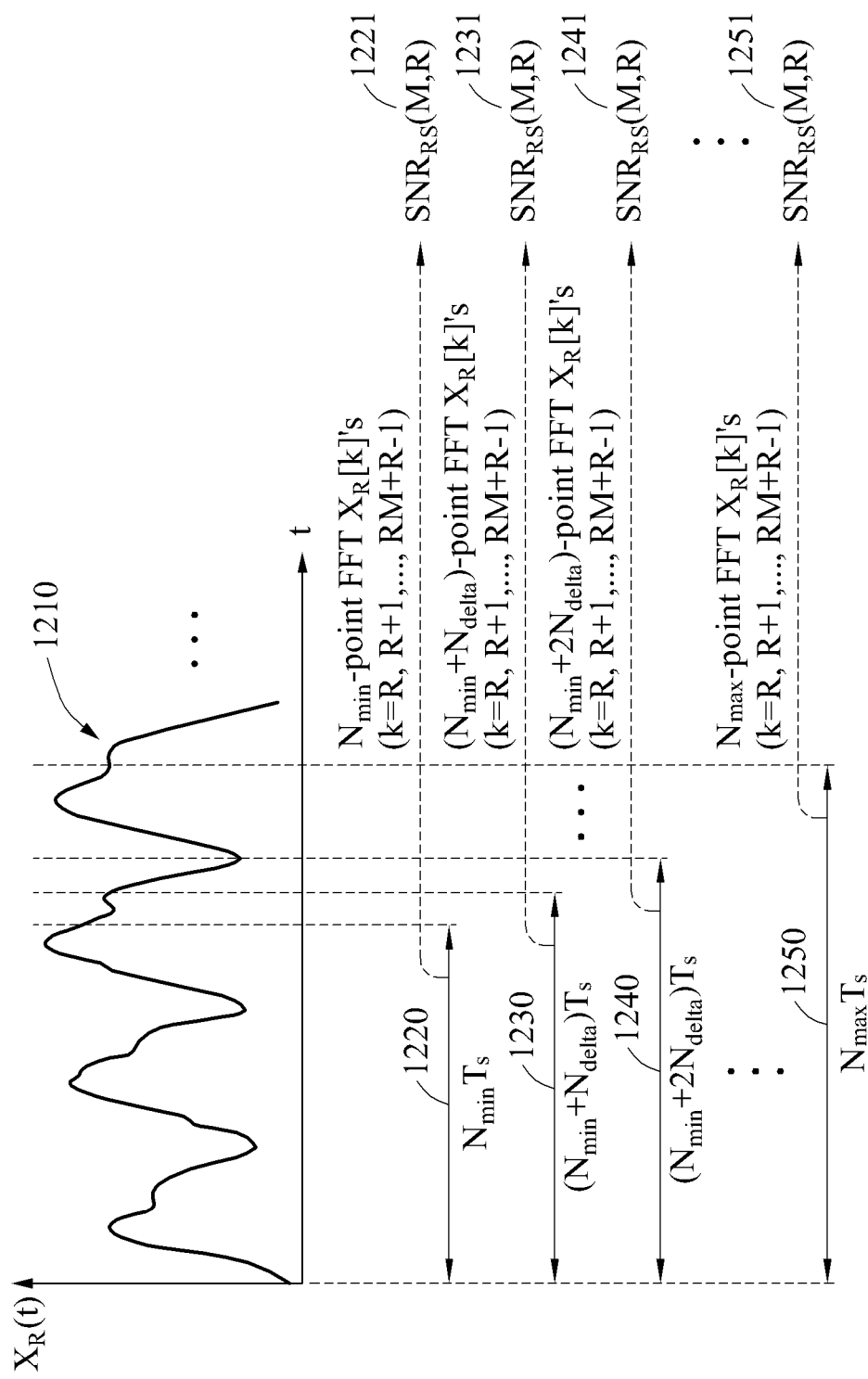
FIGS. 12 through 14 are diagrams illustrating an example of a process of calculating a quality metric.
Figure 13:
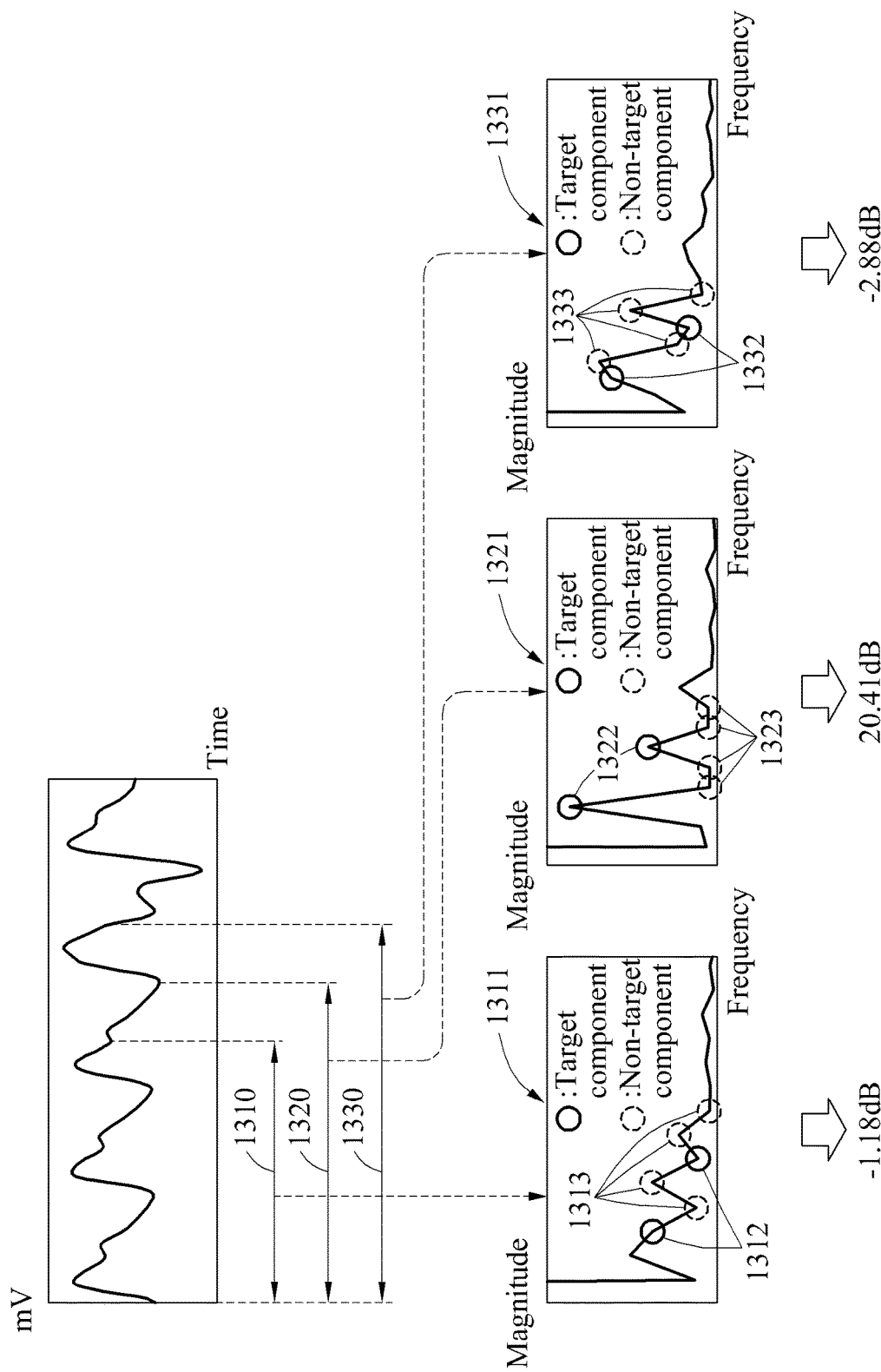
Figure 14:
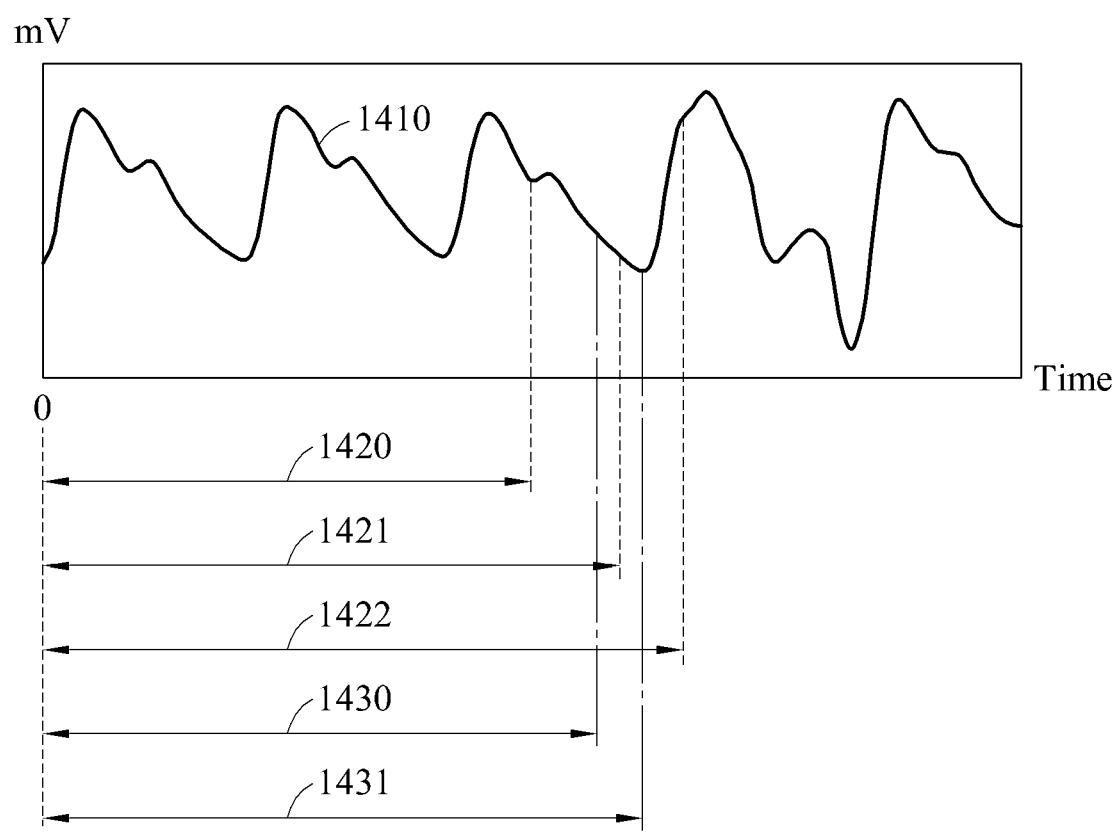

FIGS. 12 through 14 are diagrams illustrating an example of a process of calculating a quality metric.

In FIG. 12, a biosignal 1210 is illustrated. Referring to FIG. 12, the biosignal 1210 is input to a biosignal processing apparatus. The biosignal 1210 input to the biosignal processing apparatus is a signal that is sampled based on a sampling rate and passed through an analog-to-digital converter (ADC).

The biosignal processing apparatus sets a target interval. The biosignal processing apparatus sets $N_{min}$ samples to be a target interval 1220. "$T_s$" denotes a sampling interval, which is an inverse value of the sampling rate. A time length of the target interval 1220 is $N_{min}*T_s$. The biosignal processing apparatus converts the target interval 1220 to a frequency domain signal through an $N_{min}$-point FFT. The biosignal processing apparatus calculates a quality metric 1221 corresponding to the target interval 1220 based on a target component and a non-target component among frequency components of the frequency domain signal. When the quality metric 1221 is calculated, the biosignal processing apparatus changes the target interval 1220. The biosignal processing apparatus increases the number of samples of the target interval 1220 by a value of $N_{delta}$ to set a target interval 1230. A time length of the target interval 1230 is $(N_{min}+N_{delta})*T_s$.

When the target interval 1230 is set, the biosignal processing apparatus calculates a quality metric 1231 corresponding to the target interval 1230. The biosignal processing apparatus compares the quality metric 1221 to the quality metric 1231. The biosignal processing apparatus selects a greater quality metric from the quality metric 1221 and the quality metric 1231. In this example, the quality metric 1231 is assumed to be greater than the quality metric 1221.

Based on the selecting of the quality metric 1231, the biosignal processing apparatus increases the number of samples of the target interval 1230 by the value of $N_{delta}$ to set a target interval 1240, and calculates a quality metric 1241 corresponding to the target interval 1240. The biosignal processing apparatus compares the quality metric 1231 to the quality metric 1241, and selects a greater quality metric from the quality metric 1231 and the quality metric 1241. In this example, the quality metric 1241 is assumed to be greater than the quality metric 1231.

Based on the selecting of the quality metric 1241, the biosignal processing apparatus sets $N_{max}$ samples to be a target interval 1250, and calculates a quality metric 1251 corresponding to the target interval 1250. The biosignal processing apparatus compares the quality metric 1241 to the quality metric 1251, and selects a greater quality metric from the quality metric 1241 and the quality metric 1251. In this example, the quality metric 1241 is assumed to be greater than the quality metric 1251.

Thus, the quality metric 1241 and the target interval 1240 are obtained by processing the biosignal 1210.

The biosignal processing apparatus processes a plurality of biosignals using the method described with reference to FIG. 12, and obtains a maximum quality metric of each biosignal.

A value of $N_{min}$ and a value of $N_{max}$ may be preset based on a characteristic of a biosignal. For example, the respective values of $N_{min}$ and $N_{max}$ may be set based on a normal heart rate range. In addition to the normal heart rate range, the values of $N_{min}$ and $N_{max}$ may also be set based on an abnormal heart rate range that deviates from the normal heart rate range. The abnormal heart rate range may be a given value in a system.

A maximum value is identified among the quality metrics 1221, 1231, 1241, and 1251 based on waveforms of the target intervals 1220, 1230, 1240, and 1250. When a set value of a quality metric is R, and a waveform of a biosignal is repeated R times, the quality metric of the biosignal will be large. In FIG. 12, when R is 3 (R=3), the quality metric 1241 is the maximum value. Since a waveform is repeated three times in the target interval 1240, the quality metric 1241 is the maximum value. A relationship between the number of waveform repetitions of a biosignal and a quality metric will be described in detail with reference to FIG. 13.

In frequency domain analysis, the quality metric 1241 is the maximum value because a magnitude of a signal corresponding to a third frequency component and a sixth frequency component which are an integral multiple of R among frequency components of the target interval 1240 is large and a magnitude of a signal corresponding to a frequency component which is not an integral multiple of R is small. In this example, a characteristic of a quality metric based on Equations 10 through 12 is applied. Hereinafter, a detailed description will be provided with reference to FIG. 13 in which a frequency domain signal is illustrated.

In FIG. 13, a frequency domain signal 1311, a frequency domain signal 1321, and a frequency domain signal 1331 corresponding respectively to a target interval 1310, a target interval 1320, and a target interval 1330 are illustrated.

In this example, M is 2 (M=2) and R is 3 (R=3).

$$SNR_{RS}(M, R) = \frac{\sum_{m=1}^{M} |X_R[Rm]|^2}{\sum_{m=1}^{M} \sum_{l=1}^{R-1} |X_R[Rm + l]|^2} \quad (13)$$

Referring to Equation 13, a quality metric corresponding to the target interval 1310 is −1.18 decibels (dB), a quality metric corresponding to the target interval 1320 is 20.41 dB, and a quality metric corresponding to the target interval 1330 is −2.88 dB.

A frequency corresponding to a point at which a line in a graph of the frequency domain signal 1311, the frequency domain signal 1321, and the frequency domain signal 1331 changes direction is a frequency component. Since R is set to 3, a third frequency component and a sixth frequency component of the frequency domain signal 1311 are a target component. In a case of the frequency domain signal 1311, a target component signal 1312 and a non-target component signal 1313 are not distinguishable. Thus, in frequency domain analysis, a desired signal cannot be identified through the frequency domain signal 1311. Similarly, in a case of the frequency domain signal 1331, a target component signal 1332 and a non-target component signal 1333 are not distinguishable.

In a case of the frequency domain signal 1321, a target component signal 1322 and a non-target component signal 1323 are distinguishable. A magnitude of a third frequency component signal and a sixth frequency component, which are the target component signal 1322, is greater than a magnitude of another frequency component signal, which is the non-target component signal 1323. Thus, a quality metric corresponding to the target interval 1320 is greater than other quality metrics, and the desired signal can be identified through the target component. In the frequency domain analysis, the desired signal may be identified though the frequency domain signal 1321.

In one example, when the target interval 1310 is extended to be closer to the target interval 1320, a quality metric increases. When the target interval 1320 is extended to be closer to the target interval 1330, a quality metric decreases. A frequency domain signal of a target interval between the target interval 1310 and the target interval 1320 will be closer to the frequency domain signal 1321 than the frequency domain signal 1311, and thus a quality metric corresponding to the target interval between the target interval 1310 and the target interval 1320 will be greater than a quality metric corresponding to the target interval 1310. Similarly, a quality metric corresponding to a target interval between the target interval 1320 and the target interval 1330 will be greater than a quality metric corresponding to the target interval 1330.

In addition, the number of waveform occurrences of the target intervals 1310 through 1330 is associated with a quality metric. As illustrated in FIG. 13, the number of waveform repetitions in the target interval 1310 is less than three times, the number of waveform repetitions in the target interval 1320 is three times, and the number of waveform repetitions in the target interval 1330 is greater than three times. Due to the extension of the target interval 1320, the number of waveform repetitions in the target interval 1330 is greater than three times. When the number of waveform repetitions in the target interval 1320 corresponds to R, the quality metric corresponding to the target interval 1320 will be greater than the respective quality metrics of the target intervals 1310 and 1330. When the number of waveform repetitions corresponds to R, a magnitude of a target component signal will be greater than a magnitude of a non-target component signal, and thus the quality metric will be greater. Similarly, referring to FIG. 12, the number of waveform repetitions in the target interval 1240 corresponding to the quality metric 1241 is three times, and the number of waveform repetitions in other target intervals is less than or greater than three times. Since the number of waveform repetitions in the target interval 1240 corresponds to R, the quality metric 1241 is greater than other quality metrics.

Thus, the target interval 1310 may be extended to discover the target interval 1320 in which a waveform is repeated a number of times corresponding to the set value R.

The descriptions provided with reference to FIGS. 12 and 13 are also applicable to FIG. 10, and thus a more detailed explanation of FIG. 10 has been omitted.

In FIG. 14, an example of a biosignal 1410 is illustrated.

A biosignal processing apparatus sets a target interval 1420, and calculates a first quality metric corresponding to the target interval 1420. The biosignal processing apparatus extends the target interval 1420 by a first step size. For example, the biosignal processing apparatus increases the number of samples of the target interval 1420 by the first step size. When the target interval 1420 is extended, a target interval 1421 is set. The biosignal processing apparatus calculates a second quality metric corresponding to the target interval 1421, and compares the first quality metric to the second quality metric. The biosignal processing apparatus then extends the target interval 1421 by the first step size. When the target interval 1421 is extended, a target interval 1422 is set. The biosignal processing apparatus calculates a third quality metric corresponding to the target interval 1422. In this example, the second quality metric is assumed to be greatest among the first quality metric, the second quality metric, and the third quality metric.

In one example, the biosignal processing apparatus changes a target interval using the first step size, and selects any one of first changed target intervals for which the first step size is used. For the selecting, the biosignal processing apparatus uses a quality metric. In FIG. 14, the biosignal processing apparatus selects the target interval 1421 corresponding to a quality metric having a maximum value from the target intervals 1420, 1421, and 1422.

The biosignal processing apparatus changes the selected changed target interval using a second step size. The second step size may be smaller than the first step size. In FIG. 14, the biosignal processing apparatus extends or reduces the target interval 1421 by the second step size. When the target interval 1421 is reduced by the second step size, a target interval 1430 is set. When the target interval 1421 is extended by the second step size, a target interval 1431 is set. A maximum value among quality metrics corresponding respectively to the target intervals 1421, 1430, and 1431 is determined to be a maximum quality metric.

In one example, the biosignal processing apparatus processes a biosignal by changing a target interval by a first step size, and determines a directivity of a quality metric calculated based on a result of the processing. That is, the biosignal processing apparatus determines whether the quality metric increases or decreases. As illustrated in FIG. 14, the first quality metric is less than the second quality metric, and the second quality metric is greater than the third quality metric. When the target interval 1420 is extended to the target interval 1421, the quality metric increases. When the target interval 1421 is extended to the target interval 1422, the quality metric decreases. Thus, a target interval corresponding to the maximum quality metric is greater than or equal to the target interval 1421 and less than the target interval 1422. The biosignal processing apparatus extends the target interval 1421 by the second step size, and calculates a quality metric corresponding to the extended target interval.

The descriptions provided with reference to FIGS. 1 through 13 are also applicable to FIG. 14, and thus a more detailed description of FIG. 14 has been omitted.

Figure 15:
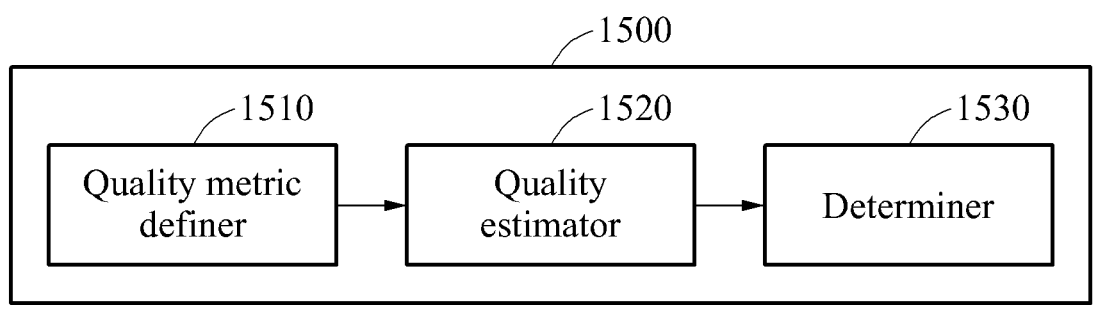
FIG. 15 is a diagram illustrating another example of a biosignal processing apparatus.

FIG. 15 is a diagram illustrating another example of a biosignal processing apparatus 1500.

Referring to FIG. 15, the biosignal processing apparatus 1500 includes a quality metric definer 1510, a quality estimator 1520, and a determiner 1530.

The quality metric definer 1510 defines a quality metric based on a target component and a non-target component of a target interval of a biosignal. The target component is a frequency component of the target interval that corresponds to a set value, and the non-target component is a frequency component of the target interval that does not correspond to the set value.

The quality metric definer 1510 converts the target interval to a frequency domain signal and defines, as the target component, a frequency component that is an integral multiple of the set value among frequency components of the frequency domain signal. In addition, the quality metric definer 1510 extracts a first number of target component signals, and a second number of non-target component signals. The second number is defined based on the first number and the set value. The quality metric definer 1510 defines the quality metric using an electric power of the extracted first number of target component signals and an electric power of the extracted second number of non-target component signals.

The quality estimator 1520 estimates qualities of the biosignals based on the quality metric. For example, the quality estimator 1520 estimates the qualities of the biosignals by obtaining respective representative quality metrics of the biosignals. Hereinafter, a method of estimating a quality of an individual biosignal among the biosignals will be described. The quality estimator 1520 obtains a plurality of quality metrics by changing either one or both of a target interval and a set value of an individual biosignal. The quality estimator 1520 obtains a maximum quality metric based on the quality metrics, and determines the maximum quality metric to be a representative quality metric. In addition, the quality estimator 1520 stores, in a memory, a target interval corresponding to the representative quality metric. Similarly, the quality estimator 1520 determines a representative quality metric of another biosignal, and stores, in the memory, a target interval corresponding to the representative quality metric.

The determiner 1530 determines a target biosignal to be monitored based on the qualities of the biosignals. In an example, the determiner 1530 determines, to be to the target biosignal to be monitored, a target interval corresponding to a maximum value of the representative quality metrics. In another example, the determiner 1530 determines whether the representative quality metric of the individual biosignal is greater than or equal to a threshold value, and determines, to be the target biosignal to be monitored, a target interval corresponding to the representative quality metric when the determiner 1530 determines that the representative quality metric of the individual biosignal is greater than or equal to the threshold value.

The determiner 1530 defines, as a preset value, a magnitude of a non-target component signal of the determined biosignal. For example, the magnitude of the non-target component signal is set to 0, thereby eliminating a noise component and other distortions of the determined biosignal.

The determiner 1530 obtains period information of the determined biosignal.

The descriptions provided with reference to FIGS. 1 through 14 are also applicable to FIG. 15, and thus a more detailed description of FIG. 15 has been omitted.

Figure 16:
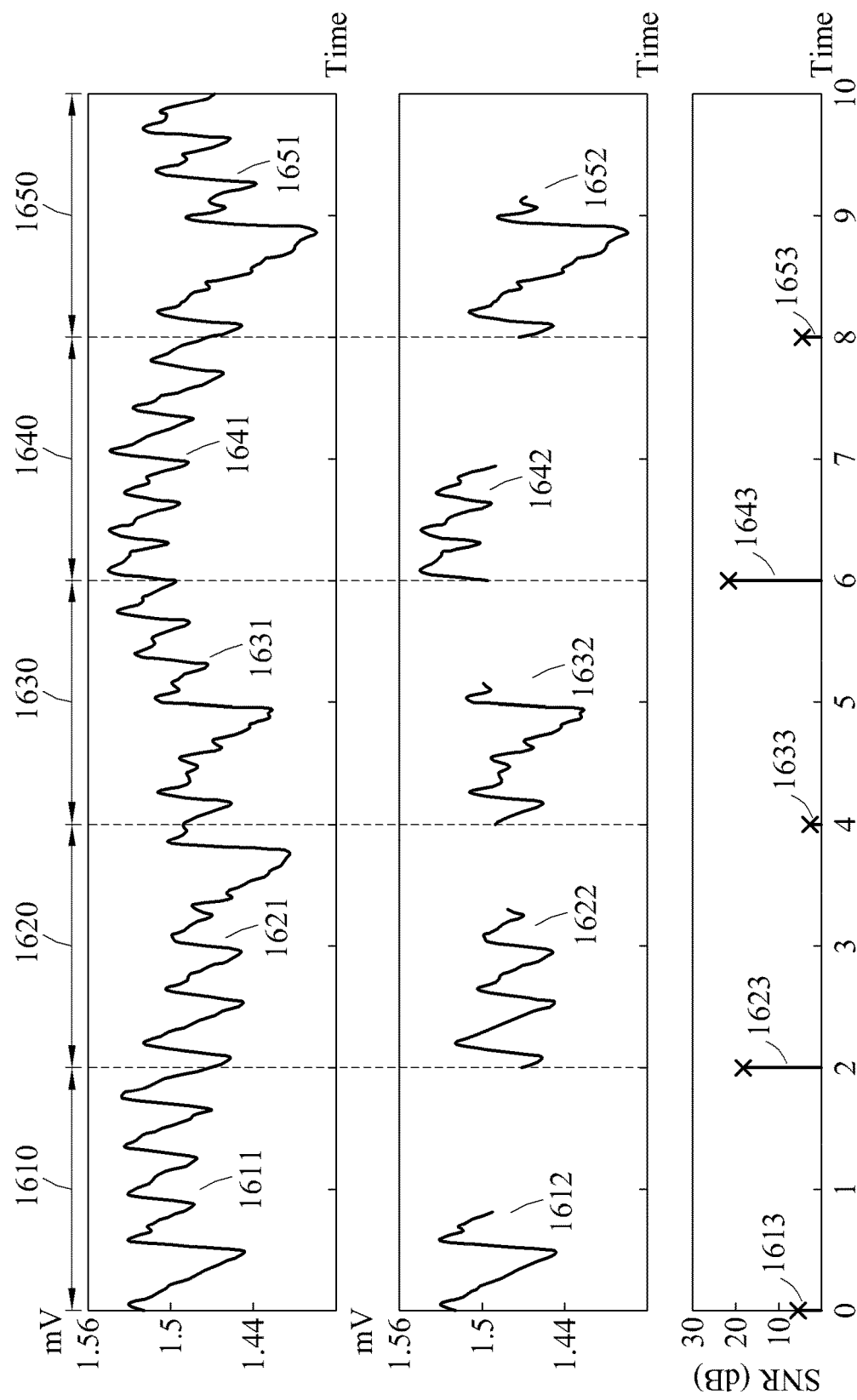
FIG. 16 is a diagram illustrating an example of a process of determining a target biosignal to be monitored among biosignals.

FIG. 16 is a diagram illustrating an example of a process of determining a target biosignal to be monitored among biosignals.

In FIG. 16, a biosignal sensed $N_{trial}$ times is assumed to be transmitted to a biosignal processing apparatus through $N_{channel}$ sensing channels. The biosignal processing apparatus processes $N_{channel}*N_{trial}$ biosignals to determine a target biosignal to be monitored.

In FIG. 16, a plurality of biosignals, for example, a biosignal 1611, a biosignal 1621, a biosignal 1631, a biosignal 1641, and a biosignal 1651, are illustrated. Although sensing channels of the biosignals 1611 through 1651 are identical, sensed time intervals of the biosignals 1611 through 1651 are different. The biosignal processing apparatus processes the biosignals 1611 through 1651 sensed in different time intervals, for example, a time interval 1610, a time interval 1620, a time interval 1630, a time interval 1640, and a time interval 1650, and determines the target biosignal to be monitored based on a result of the processing.

When an SNR is a maximum quality metric, for example, a maximum quality metric 1613, a maximum quality metric 1623, a maximum quality metric 1633, a maximum quality metric 1643, and a maximum quality metric 1653, target intervals, for example, a target interval 1612, a target interval 1622, a target interval 1632, a target interval 1642, and a target interval 1652, correspond to the maximum quality metrics 1613 through 1653, respectively. In this example, quality metrics are calculated with a set value being 3.

The biosignal processing apparatus selects a maximum quality metric having a maximum value among the maximum quality metrics 1613 through 1653. As illustrated in FIG. 16, the maximum quality metric 1643 has a maximum value among the maximum quality metrics 1613 through 1653, and thus the biosignal processing apparatus determines the target interval 1642 corresponding to the maximum quality metric 1643 to be the target biosignal to be monitored.

As described in the foregoing, the number of waveform repetitions in the target interval 1642 corresponds to the set value, and the number of waveform repetitions in other target intervals does not correspond to the set value. The number of waveform repetitions of the target biosignal to be monitored among the biosignals corresponds to the set value. The biosignal processing apparatus obtains period information of the target interval 1642 by dividing a time length of the target interval 1642 by the set value. The biosignal processing apparatus estimates health information of a user using the period information and transmits the period information to an external monitoring device.

In one example, the biosignal processing apparatus performs user authentication based on a waveform pattern of the determined target biosignal to be monitored. For example, the biosignal processing apparatus compares a waveform pattern of the target interval 1642 to a prestored waveform pattern, and authenticates the user when a result of the comparing indicates that the waveform pattern is similar to or corresponds to the prestored waveform pattern.

The descriptions provided with reference to FIGS. 1 through 15 are also applicable to FIG. 16, and thus a more detailed description of FIG. 16 has been omitted.

Figure 17:
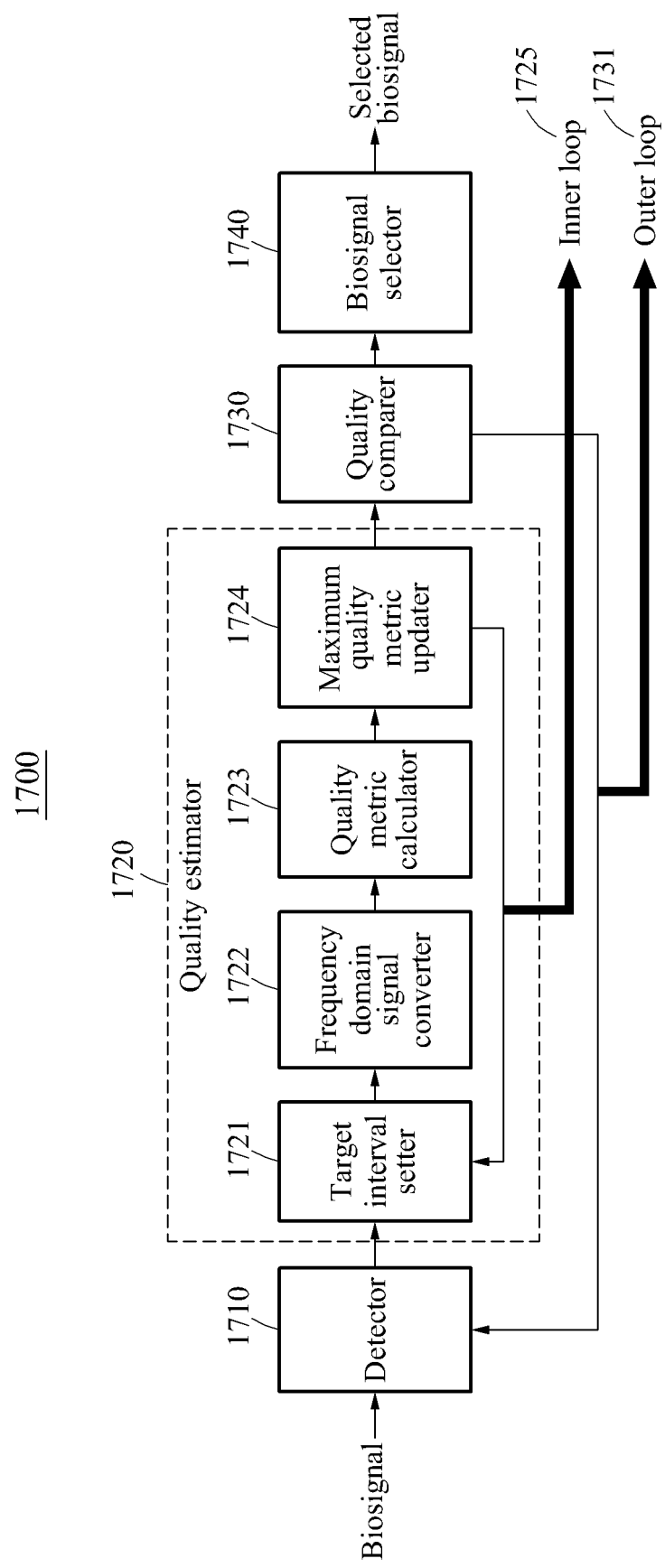
FIG. 17 is a diagram illustrating another example of a biosignal processing apparatus.

FIG. 17 is a diagram illustrating another example of a biosignal processing apparatus 1700.

Referring to FIG. 17, the biosignal processing apparatus 1700 includes a detector 1710, a quality estimator 1720, a quality comparer 1730, and a biosignal selector 1740.

The detector 1710 senses a biosignal. For example, the detector 1710 includes a photoplethysmogram (PPG) sensor, and senses a PPG signal of a user.

The detector 1710 senses a biosignal of the user through a plurality of sensing channels during a plurality of time intervals. For example, $N_{channel}$ sensing channels are in contact with a body of the user, and a biosignal is sensed $N_{trial}$ times through each sensing channel. In such an example, the detector 1710 senses $N_{channel}*N_{trial}$ biosignals. The detector 1710 transmits, to the quality estimator 1720, a first biosignal among the $N_{channel}*N_{trial}$ biosignals.

The quality estimator 1720 estimates a quality of the first biosignal.

The quality estimator 1720 includes a target interval setter 1721, a frequency domain signal converter 1722, a quality metric calculator 1723, and a maximum quality metric updater 1724.

The target interval setter 1721 sets a target interval of the first biosignal. For example, the target interval setter 1721 sets, to be the target interval, a biosignal included between a first time point and a second time point of the first biosignal. Concisely, the target interval setter 1721 sets the target interval from a first sample to an $N_{min}$-th sample. $N_{min}$ is a preset value. Alternatively, the target interval setter 1721 sets the target interval from an n-th sample to the $N_{min}$-th sample. A value of n is less than the value of $N_{min}$. The target intervals described in the foregoing are provided merely as examples, and thus the target interval is not limited to these examples.

The frequency domain signal converter 1722 converts the target interval to a frequency domain signal. For example, the frequency domain signal converter 1722 converts the target interval to the frequency domain signal through an FFT or a DFT. In addition, the frequency domain signal converter 1722 may scale a magnitude and/or a frequency of the frequency domain signal.

The quality metric calculator 1723 calculates a quality metric of the frequency domain signal. A frequency component of the frequency domain signal that corresponds to a set value is referred to as a target component, and a frequency component of the frequency domain signal that does not correspond to the set value is referred to as a non-target component. The quality metric calculator 1723 calculates the quality metric of the frequency domain signal based on the target component and the non-target component.

The maximum quality metric updater 1724 updates a maximum quality metric of the first biosignal. A quality metric currently calculated through an inner loop 1725 is a first quality metric. The maximum quality metric updater 1724 compares the first quality metric to a previous quality metric previously calculated through the inner loop 1725, and determines which one of the first quality metric and the previous quality metric has a greater value. In this example, the first quality metric is assumed to be greater than the previous quality metric. When the greater value is determined, the maximum quality metric updater 1724 transfers a feedback signal to the target interval setter 1721.

The target interval setter 1721 updates the target interval of the first biosignal based on the feedback signal. As described in the foregoing, since the target interval spans from the first sample to the $N_{min}$-th sample, the target interval setter 1721 updates the target interval to span from the first sample to an $N_{min}+N_{delta}$-th sample.

The frequency domain signal converter 1722 converts the updated target interval to a frequency domain signal, and the quality metric calculator 1723 calculates a quality metric corresponding to the updated target interval. The quality metric corresponding to the updated target interval is a second quality metric, and the maximum quality metric updater 1724 compares the first quality metric to the second quality metric to determine which one of the first quality metric to the second quality metric has a greater value. When the maximum quality metric updater 1724 determines that the second quality metric is greater than the first quality metric, the maximum quality metric updater 1724 updates a maximum quality metric of the first biosignal.

When the feedback signal is transferred to the target interval setter 1721, the target interval is updated to a target interval from the first sample to an $N_{max}$-th sample, and a quality metric corresponding to the target interval from the first sample to the $N_{max}$-th sample may be calculated, and thus the maximum quality metric is updated. In this example, a value of $N_{max}$ is a preset value.

Based on the inner loop 1725, operations of the target interval setter 1721, the frequency domain signal converter 1722, the quality metric calculator 1723, and the maximum quality metric updater 1724 are repeated. Through repetition of the operations, the quality estimator 1720 determines the maximum quality metric of the first biosignal, and stores, in a memory, a target interval corresponding to the maximum quality metric. The quality estimator 1720 transfers the maximum quality metric of the first biosignal to the quality comparer 1730. The maximum quality metric of the first biosignal is referred to as a first maximum quality metric.

In one example, the quality comparer 1730 compares the first maximum quality metric to a previous maximum quality metric input through an outer loop 1731 to determine which one of the first maximum quality metric and the previous maximum quality metric has a greater value. In this example, the first maximum quality metric is assumed to be greater than the previous maximum quality metric. When the quality comparer 1730 determines that the first maximum quality metric has the greater value, the quality comparer 1730 generates a feedback signal and transmits the feedback signal to the detector 1710.

In another example, the quality comparer 1730 compares the first maximum quality metric to a threshold value. When the quality comparer 1730 determines that the first maximum quality metric is greater than or equal to the threshold value, the quality comparer 1730 terminates the outer loop 1731 and transfers the first maximum quality metric to the biosignal selector 1740. When the quality comparer 1730 determines that the first maximum quality metric is less than the threshold value, the quality comparer 1730 generates a feedback signal and transmits the feedback signal to the detector 1710.

The detector 1710 transfers a second biosignal among the sensed $N_{channel}*N_{trial}$ biosignals to the quality estimator 1720. Based on the inner loop 1725, the quality estimator 1720 determines a maximum quality metric of the second biosignal, and stores, in the memory, a target interval corresponding to the maximum quality metric. The quality estimator 1720 transfers the maximum quality metric of the second biosignal to the quality comparer 1730. In this example, the maximum quality metric of the second biosignal is referred to as a second maximum quality metric. The quality comparer 1730 compares the first maximum quality metric to the second maximum quality metric to determine which one of the first maximum quality metric and the second maximum quality metric has a greater value. When the greater value is determined, the outer loop 1731 is repeated.

When the outer loop 1731 is repeated $N_{channel}*N_{trial}$ times, respective maximum quality metrics of the $N_{channel}*N_{trial}$ biosignals are determined, and respective target intervals corresponding to the maximum quality metrics are stored in the memory. When the repetition of the outer loop 1731 terminates, a maximum value among the $N_{channel}*N_{trial}$ maximum quality metrics is transferred to the biosignal selector 1740. When a maximum quality metric of each of the $N_{channel}*N_{trial}$ biosignals is less than the threshold value, the quality comparer 1730 generates a feedback signal providing an instruction of sensing a biosignal and transmits the feedback signal to the detector 1710. The detector 1710 senses a biosignal.

The biosignal selector 1740 determines, to be a target biosignal to be monitored, a target interval corresponding to the maximum value.

The descriptions provided with reference to FIGS. 1 through 16 are also applicable to FIG. 17, and thus a more detailed description of FIG. 17 has been omitted.

Figure 18:
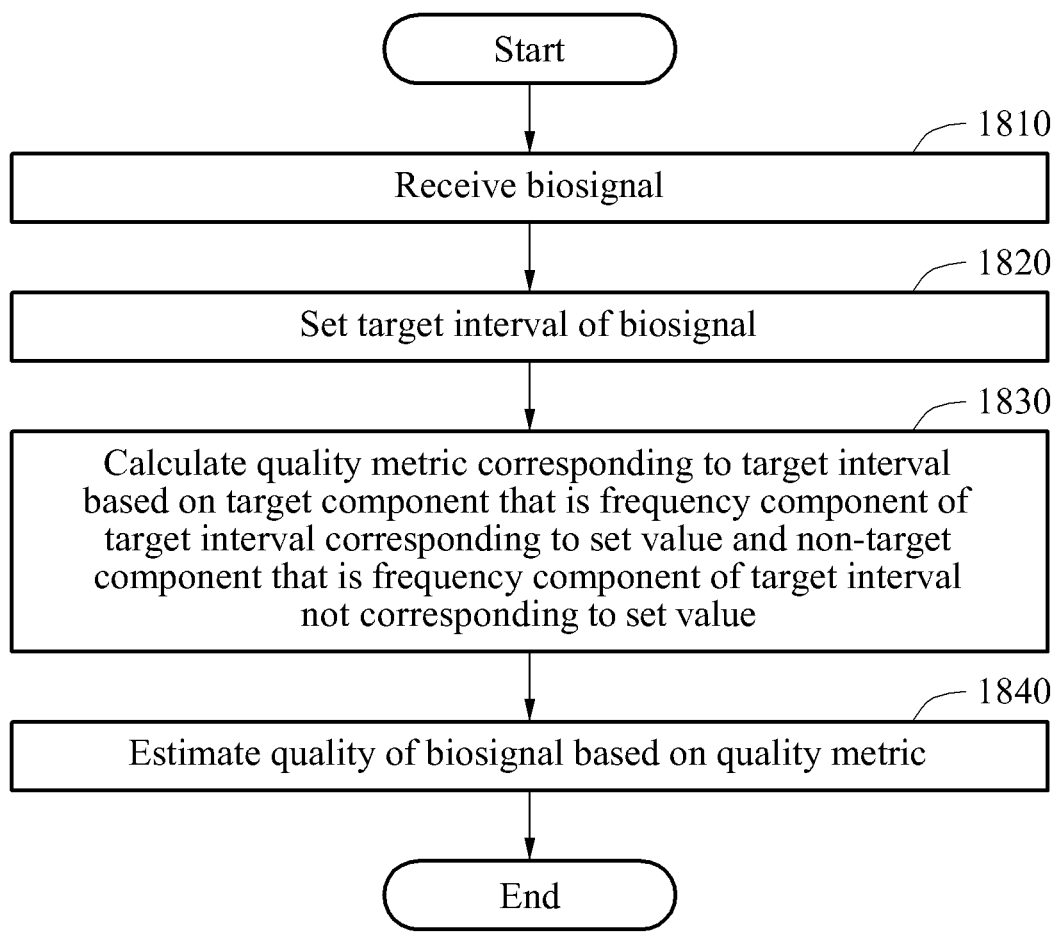
FIG. 18 is a flowchart illustrating an example of a biosignal processing method.

FIG. 18 is a flowchart illustrating an example of a biosignal processing method. The biosignal processing method to be described with reference to FIG. 18 may be performed by a biosignal processing apparatus.

Referring to FIG. 18, in operation 1810, the biosignal processing apparatus receives a biosignal. The biosignal processing apparatus may receive the biosignal from a sensor.

In operation 1820, the biosignal processing apparatus sets a target interval of the biosignal.

In operation 1830, the biosignal processing apparatus calculates a quality metric corresponding to the target interval based on a target component and a non-target component. The target component is a frequency component of the target interval that corresponds to a set value, and the non-target component is a frequency component of the target interval that does not correspond to the set value.

In operation 1840, the biosignal processing apparatus estimates a quality of the biosignal based on the quality metric.

The descriptions provided with reference to FIGS. 1 through 17 are also applicable to FIG. 18, and thus a more detailed description of FIG. 18 has been omitted.

Figure 19:
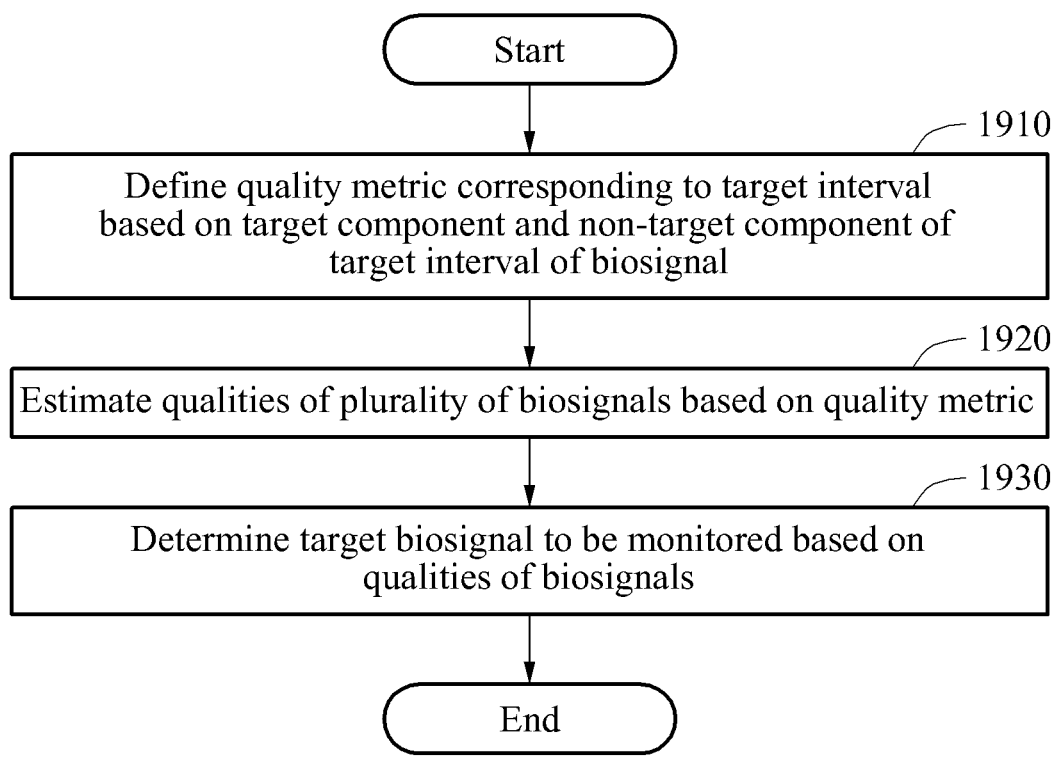
FIG. 19 is a flowchart illustrating another example of a biosignal processing method.

FIG. 19 is a flowchart illustrating another example of a biosignal processing method. The biosignal processing method to be described with reference to FIG. 19 may be performed by a biosignal processing apparatus.

Referring to FIG. 19, in operation 1910, the biosignal processing apparatus defines a quality metric corresponding to a target interval based on a target component and a non-target component of the target interval of an individual biosignal.

In operation 1920, the biosignal processing apparatus estimates qualities of a plurality of biosignals based on the quality metric.

In operation 1930, the biosignal processing apparatus determines a target biosignal to be monitored based on the qualities of the biosignals.

The descriptions provided with reference to FIGS. 1 through 17 are also applicable to FIG. 19, and thus a more detailed description of FIG. 19 has been omitted.

Figure 20:
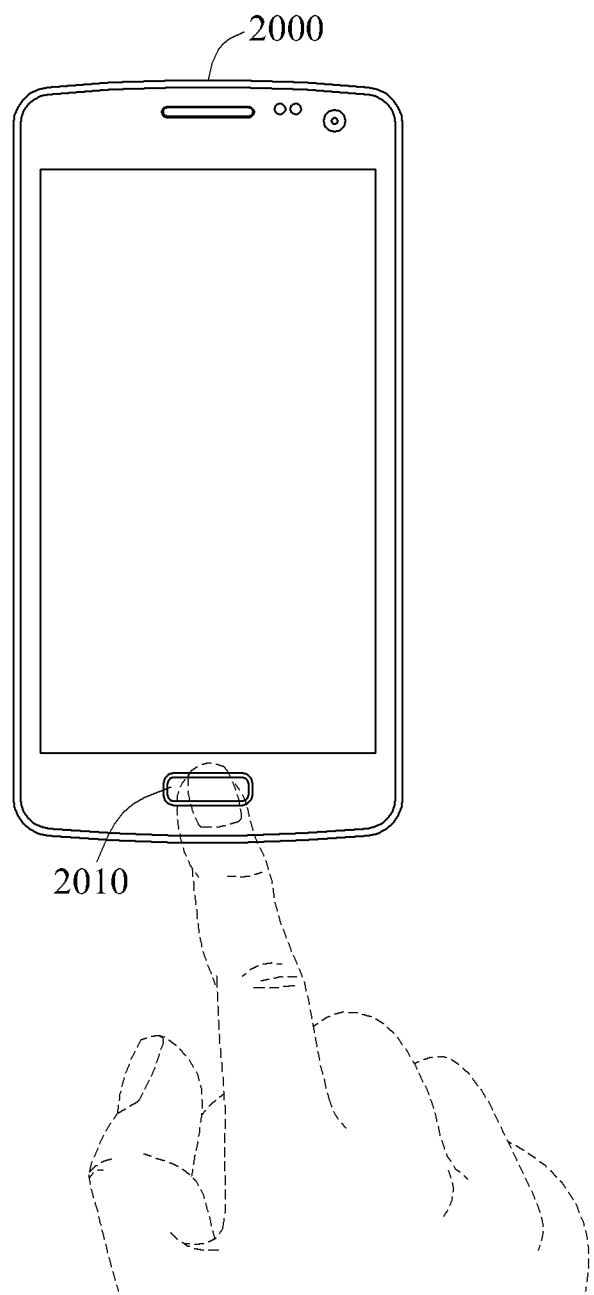
FIG. 20 illustrates an example of a terminal including a biosignal processing apparatus.

FIG. 20 illustrates an example of a terminal 2000 including a biosignal processing apparatus.

Referring to FIG. 20, the terminal 2000 includes a sensor 2010. The sensor 2010 includes a plurality of sensors, and senses various biosignals of a user. For example, the sensor 2010 senses a PPG signal, a body temperature, and a bio-impedance.

The sensor 2010 senses a biosignal using a plurality of sensing channels. In addition, the sensor 2010 senses a biosignal in a plurality of time intervals. For example, in a case of N sensing channels and M time intervals, the number of biosignals sensed by the sensor 2010 is N*M.

In the example illustrated in FIG. 20, the sensor 2010 senses a biosignal at a fingertip of the user. However, the sensor 2010 may be located in another portion of the terminal 2000, for example, on a rear and a side of the terminal 2000, and sense a biosignal by contacting another body portion of the user that is not a finger of the user.

The biosignals sensed by the sensor 2010 are transferred to the biosignal processing apparatus included in the terminal 2000. The biosignals transferred to the biosignal processing apparatus are of a same type. The biosignal processing apparatus processes each of the biosignals. The biosignal processing apparatus selects a first maximum quality metric from quality metrics of a first biosignal, and selects a second maximum quality metric from quality metrics of a second biosignal. The first biosignal and the second biosignal are biosignals of a same type. The biosignal processing apparatus selects a maximum value among the first maximum quality metric and the second maximum quality metric, and determines, to be a target biosignal to be monitored, a target interval corresponding to the maximum value.

The terminal 2000 obtains health information associated with a health condition of the user using the target biosignal to be monitored. For example, the terminal 2000 obtains a heart rate of the user. The terminal 2000 transfers, to an external monitoring device, the target biosignal to be monitored.

By performing the biosignal processing described in the foregoing, a biosignal having a desirable quality may be used to monitor the health condition of the user.

The descriptions provided with reference to FIGS. 1 through 19 are also applicable to FIG. 20, and thus a more detailed description of FIG. 20 has been omitted.

Figure 21:
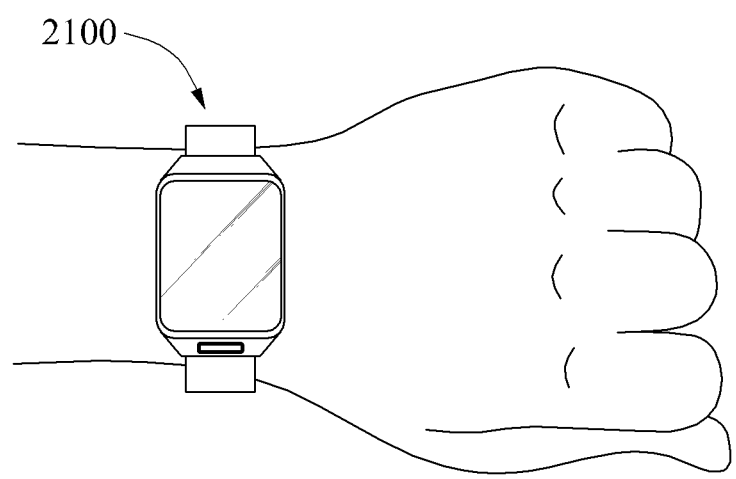
FIG. 21 illustrates an example of a wearable device including a biosignal processing apparatus.

FIG. 21 illustrates an example of a wearable device 2100 including a biosignal processing apparatus.

Referring to FIG. 21, the wearable device 2100 includes a sensor (not shown). Although the wearable device 2100 is illustrated as a watch-type wearable device in FIG. 21, the wearable device 2100 not limited to the illustrated watch-type wearable device.

The wearable device 2100 senses a biosignal of a user through the sensor. The sensor contacts physically different portions of a wrist of the user, and senses a biosignal at physically different locations. For example, the sensor senses a biosignal at three to six physically different locations. The biosignal processing apparatus included in the wearable device 2100 processes the sensed biosignal.

When the wearable device 2100 is not in a stable contact with the user, or the user wearing the wearable device 2100 performs numerous movements, the wearable device 2100 may sense and process a distorted biosignal. For example, the wearable device 2100 may sense and process the distorted biosignal illustrated in FIG. 2B. When a distorted biosignal is used to monitor the health of the user, a false result may be derived therefrom.

As in a case of the terminal 2000 illustrated in FIG. 20, the wearable device 2100 processes a plurality of biosignals and extracts a biosignal having a desirable quality from the biosignals. Since the biosignal processing apparatus uses biosignals sensed through a plurality of sensing channels and/or in a plurality of time slots, a biosignal distorted due to an unstable environment or other reasons will not be used to monitor the health of the user, and only a biosignal sensed in a stable environment will be used to monitor the health of the user. In addition, a biosignal processing method described herein includes selecting a biosignal having a desirable quality from a plurality of biosignals, and thus is robust against an unstable environment or a mobile environment.

Although not illustrated in FIG. 21, the biosignal processing apparatus may be included in a sensor to be attached to a body of a user.

The sensor, the wearable device 2100, and a user terminal may form a wireless body area network (WBAN). The sensor and/or the wearable device 2100 sense a plurality of biosignals, and select a biosignal having a desirable quality from the biosignals. The sensor and/or the wearable device 2100 transmit the selected biosignal to the terminal. The terminal obtains information associated with health of a user by transmitting the selected biosignal to an external monitoring device through the Internet or analyzing the selected biosignal.

The descriptions provided with reference to FIGS. 1 through 19 are also applicable to FIG. 21, and thus a more detailed description of FIG. 21 has been omitted.

The biosignal processing apparatus 1100, the communication interface 1110, and the processor 1120 illustrated in FIG. 11, the biosignal processing apparatus 1500, the quality metric definer 1510, the quality estimator 1520, and the determiner 1530 illustrated in FIG. 15, and the biosignal processing apparatus 1700, the detector 1710, the quality estimator 1720, the target interval setter 1721, the frequency domain signal converter 1722, the quality metric calculator 1723, the maximum quality metric updater 1724, the quality comparer 1730, and the biosignal selector 1740 illustrated in FIG. 17 that perform the operations described herein with respect to FIGS. 4-21 are implemented by hardware components. Examples of hardware components include controllers, sensors, generators, drivers, memories, comparators, arithmetic logic units, adders, subtractors, multipliers, dividers, integrators, and any other electronic components known to one of ordinary skill in the art. In one example, the hardware components are implemented by computing hardware, for example, by one or more processors or computers. A processor or computer is implemented by one or more processing elements, such as an array of logic gates, a controller and an arithmetic logic unit, a digital signal processor, a microcomputer, a programmable logic controller, a field-programmable gate array, a programmable logic array, a microprocessor, or any other device or combination of devices known to one of ordinary skill in the art that is capable of responding to and executing instructions in a defined manner to achieve a desired result. In one example, a processor or computer includes, or is connected to, one or more memories storing instructions or software that are executed by the processor or computer. Hardware components implemented by a processor or computer execute instructions or software, such as an operating system (OS) and one or more software applications that run on the OS, to perform the operations described herein with respect to FIGS. 4-21. The hardware components also access, manipulate, process, create, and store data in response to execution of the instructions or software. For simplicity, the singular term "processor" or "computer" may be used in the description of the examples described herein, but in other examples multiple processors or computers are used, or a processor or computer includes multiple processing elements, or multiple types of processing elements, or both. In one example, a hardware component includes multiple processors, and in another example, a hardware component includes a processor and a controller. A hardware component has any one or more of different processing configurations, examples of which include a single processor, independent processors, parallel processors, single-instruction single-data (SISD) multiprocessing, single-instruction multiple-data (SIMD) multiprocessing, multiple-instruction single-data (MISD) multiprocessing, and multiple-instruction multiple-data (MIMD) multiprocessing.

The methods illustrated in FIGS. 18 and 19 that perform the operations described herein with respect to FIGS. 4-21 are performed by computing hardware as described above executing instructions or software to perform the operations described herein.

Instructions or software to control a processor or computer to implement the hardware components and perform the methods as described above are written as computer programs, code segments, instructions or any combination thereof, for individually or collectively instructing or configuring the processor or computer to operate as a machine or special-purpose computer to perform the operations performed by the hardware components and the methods as described above. In one example, the instructions or software include machine code that is directly executed by the processor or computer, such as machine code produced by a compiler. In another example, the instructions or software include higher-level code that is executed by the processor or computer using an interpreter. Programmers of ordinary skill in the art can readily write the instructions or software based on the block diagrams and the flow charts illustrated in the drawings and the corresponding descriptions in the specification, which disclose algorithms for performing the operations performed by the hardware components and the methods as described above.

The instructions or software to control a processor or computer to implement the hardware components and perform the methods as described above, and any associated data, data files, and data structures, are recorded, stored, or fixed in or on one or more non-transitory computer-readable storage media. Examples of a non-transitory computer-readable storage medium include read-only memory (ROM), random-access memory (RAM), flash memory, CD-ROMs, CD-Rs, CD+Rs, CD-RWs, CD+RWs, DVD-ROMs, DVD-Rs, DVD+Rs, DVD-RWs, DVD+RWs, DVD-RAMs, BD-ROMs, BD-Rs, BD-R LTHs, BD-REs, magnetic tapes, floppy disks, magneto-optical data storage devices, optical data storage devices, hard disks, solid-state disks, and any device known to one of ordinary skill in the art that is capable of storing the instructions or software and any associated data, data files, and data structures in a non-transitory manner and providing the instructions or software and any associated data, data files, and data structures to a processor or computer so that the processor or computer can execute the instructions. In one example, the instructions or software and any associated data, data files, and data structures are distributed over network-coupled computer systems so that the instructions and software and any associated data, data files, and data structures are stored, accessed, and executed in a distributed fashion by the processor or computer.

While this disclosure includes specific examples, it will be apparent to one of ordinary skill in the art that various changes in form and details may be made in these examples without departing from the spirit and scope of the claims and their equivalents. The examples described herein are to be considered in a descriptive sense only, and not for purposes of limitation. Descriptions of features or aspects in each example are to be considered as being applicable to similar features or aspects in other examples. Suitable results may be achieved if the described techniques are performed in a different order, and/or if components in a described system, architecture, device, or circuit are combined in a different manner, and/or replaced or supplemented by other components or their equivalents. Therefore, the scope of the disclosure is defined not by the detailed description, but by the claims and their equivalents, and all variations within the scope of the claims and their equivalents are to be construed as being included in the disclosure.

What is claimed is:

1. A biosignal processing apparatus in a mobile device, the apparatus comprising:
   a communication interface configured to receive a first biosignal; and
   a processor configured to:
      set a target interval in the first biosignal,
      calculate a first quality metric corresponding to the target interval of the first biosignal based on a target component that is a frequency component, among frequency components within the target interval, corresponding to a set value and based on a non-target component that is another frequency component, among the frequency components within the target interval, not corresponding to the set value,
      change the target interval,
      calculate a second quality metric corresponding to the changed target interval based on the target component within the changed target interval and the non-target component within the changed target interval,
      select a greater quality metric from among the first quality metric and the second quality metric,
      estimate a quality of the first biosignal based on the selected quality metric, and
      in response to the first biosignal being selected based on the estimated quality, determine health information of a user based on the first biosignal.

2. The apparatus of claim 1, wherein the processor is further configured to convert the first biosignal to a frequency domain signal, and define, as the target component, the frequency component that is an integral multiple of the set value among the frequency components in the frequency domain signal.

3. The apparatus of claim 1, wherein the processor is further configured to extract from the target interval a first total number of signals corresponding to the target component, and extract from the target interval a second total number of signals corresponding to the non-target component; and
   the second total number is defined based on the first total number and the set value.

4. The apparatus of claim 3, wherein the processor is further configured to calculate the first quality metric based on an electric power of the extracted first number of signals and an electric power of the extracted second number of signals.

5. The apparatus of claim 1, wherein the processor is further configured to determine one of the target interval and the changed target interval to be a target biosignal to be monitored, and define a magnitude of a signal corresponding to the non-target component of the target interval to be a preset value.

6. The apparatus of claim 1, wherein the processor is further configured to obtain period information of a target biosignal to be monitored.

7. The apparatus of claim 1, wherein the first quality metric that is calculated when a waveform is repeated a number of times equal to the set value in the target interval is greater than the first quality metric that is calculated when the waveform is not repeated a number of times equal to the set value in the target interval.

8. The apparatus of claim 1, wherein the target component is a frequency component that is an integral multiple of the set value, and the non-target component is a frequency component that is not an integral multiple of the set value.

9. A biosignal processing method implemented by a processing apparatus in a mobile device, the method comprising:
   receiving a biosignal;
   setting a target interval in the biosignal;
   calculating a first quality metric corresponding to the target interval of the biosignal based on a target component that is a frequency component, among frequency components within the target interval, corresponding to a set value and based on a non-target component that is another frequency component, among the frequency components within the target interval, not corresponding to the set value;
   changing the target interval,
   calculating a second quality metric corresponding to the changed target interval based on the target component within the changed target interval and the non-target component within the changed target interval, selecting a greater quality metric from among the first quality metric and the second quality metric;

estimating a quality of the biosignal based on the selected quality metric; and in response to the biosignal being selected based on the estimated quality, determining health information of a user based on the selected biosignal.

10. A biosignal processing method implemented by a processing apparatus in a mobile device, the method comprising:

receiving a biosignal;

selecting a plurality of target intervals in the biosignal;

calculating quality metrics respectively corresponding to the target intervals of the biosignal;

determining a maximum quality metric among the quality metrics;

determining the target interval corresponding to the maximum quality metric to be a biosignal to be monitored, and determining health information of a user based on the determined target interval, wherein the quality metrics represent an estimate of a quality of the biosignal, and wherein the quality metrics are a ratio between a sum of electric powers of one or more target component signals and a sum of electric powers of one or more non-target component signals.

11. The method of claim 10, wherein the setting of the plurality of target intervals of the biosignal comprises:

setting a first target interval;

changing the first target interval by a first step size at least once to obtain at least one first changed target interval;

selecting one of the first target interval and the at least one first changed target interval having a maximum quality metric among quality metrics calculated for the first target interval and each of the at least one first changed target interval;

changing the selected target interval at least once by a second step size smaller than the first step size to obtain at least one second changed target interval.

12. The method of claim 11, wherein the determining of a maximum quality metric among the quality metrics comprises determining a maximum quality metric among quality metrics calculated for the selected target interval and each of the at least one second changed target interval to be the maximum quality metric among the quality metrics.

13. The method of claim 10, wherein the calculating of the quality metrics comprises calculating each of the quality metrics based on at least one target component of a corresponding one of the target intervals and at least one non-target component of the corresponding one of the target intervals.

14. The method of claim 13, wherein each of the at least one target component is a frequency component corresponding to an integral multiple of a set value; and each of the at least one non-target component is a frequency component not corresponding to an integral multiple of the set value.

15. The method of claim 14, wherein the set value is an integer $R \geq 2$;

a total number of the at least one target component is an integer $M \geq 1$; and a total number of the at least one non-target component is $M*(R-1)$.

16. A biosignal processing apparatus in a mobile device, the apparatus comprising:

a communication interface configured to receive a first biosignal; and a processor configured to:

select a target interval in the first biosignal, calculate a first quality metric corresponding to the target interval of the first biosignal based on a target component that is a frequency component, among frequency components within the target interval, corresponding to a set value and based on a non-target component that is another frequency component, among the frequency components within the target interval, not corresponding to the set value, change the set value after the calculating of the first quality metric, and calculate a second quality metric different from the first quality metric based on the changed set value;

selecting a maximum quality metric from among the calculated first quality metric and the calculated second quality metric;

estimate a quality of the first biosignal based on the selected maximum quality metric, and in response to the first biosignal being selected based on the estimated quality, determine health information of a user based on the first biosignal.

* * * * *